(12) United States Patent
Yehya

(10) Patent No.: US 12,594,524 B2
(45) Date of Patent: *Apr. 7, 2026

(54) SYSTEM AND METHOD FOR CONCENTRATING GAS

(71) Applicant: Ventec Life Systems, Inc., Bothell, WA (US)

(72) Inventor: Haneen Y. Yehya, Parma, OH (US)

(73) Assignee: VENTEC LIFE SYSTEMS, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/418,447

(22) Filed: Jan. 22, 2024

(65) Prior Publication Data

US 2024/0157289 A1 May 16, 2024

Related U.S. Application Data

(63) Continuation of application No. 17/376,253, filed on Jul. 15, 2021, now Pat. No. 11,931,689.
(Continued)

(51) Int. Cl.
*B01D 53/30* (2006.01)
*A61M 16/10* (2006.01)
(Continued)

(52) U.S. Cl.
CPC ........... *B01D 53/30* (2013.01); *B01D 53/047* (2013.01); *G05B 13/048* (2013.01);
(Continued)

(58) Field of Classification Search
CPC ................. B01D 53/30; B01D 53/047; B01D 2253/108; B01D 2256/12;
(Continued)

(56) References Cited

U.S. PATENT DOCUMENTS

| | | | |
|---|---|---|---|
| 3,483,677 A | 12/1969 | Herbert | |
| 3,494,296 A | 2/1970 | Gluntz | |

(Continued)

FOREIGN PATENT DOCUMENTS

| | | | |
|---|---|---|---|
| AU | 1999015998 A | 8/1999 | |
| AU | 200072682 A1 | 5/2001 | |

(Continued)

OTHER PUBLICATIONS

US 6,979,301 B2, 12/2005, Van Brunt et al. (withdrawn)

(Continued)

*Primary Examiner* — Ronald D Hartman, Jr.
(74) *Attorney, Agent, or Firm* — Calfee, Halter & Griswold LLP

(57) ABSTRACT

Embodiments of gas concentrating systems and methods are provided. These systems and methods comprise configuration of hardware and software components to monitor various sensors associated the systems and methods of concentrating gas as described herein. These hardware and software components are further configured to utilize information obtained from sensors throughout the system to perform certain data analysis tasks. Through analysis, the system may, for example, calculate a time to failure for one or more system components, generate alarms to warn a user of pending component failure, modify system settings to improve functionality in differing environmental conditions, modify system operation to conserve energy, and/or determine optimal setting configurations based on sensor feedback.

30 Claims, 10 Drawing Sheets

Related U.S. Application Data

(60) Provisional application No. 63/052,869, filed on Jul. 16, 2020.

(51) Int. Cl.
B01D 53/047 (2006.01)
G05B 13/04 (2006.01)
G05B 23/02 (2006.01)

(52) U.S. Cl.
CPC ....... G05B 23/0254 (2013.01); G05B 23/027 (2013.01); A61M 16/101 (2014.02); B01D 2253/108 (2013.01); B01D 2256/12 (2013.01); B01D 2257/102 (2013.01); B01D 2257/502 (2013.01); B01D 2257/504 (2013.01); B01D 2257/80 (2013.01); B01D 2259/40009 (2013.01); B01D 2259/402 (2013.01); B01D 2259/4533 (2013.01); B01D 2259/4541 (2013.01)

(58) Field of Classification Search
CPC ........ B01D 2257/102; B01D 2257/502; B01D 2257/504; B01D 2257/80; B01D 2259/402; B01D 2259/4541; G05B 15/02; G05B 13/048; G05B 23/0254; G05B 23/027; G05B 20/02; G05B 23/021; G05B 23/022; A61M 16/08; A61M 2208/06
USPC ......................................... 700/275
See application file for complete search history.

(56) References Cited

U.S. PATENT DOCUMENTS

| | | | |
|---|---|---|---|
| 3,530,649 A | 9/1970 | Porsch et al. | |
| 3,602,527 A | 8/1971 | Goetz et al. | |
| 3,608,833 A | 9/1971 | Hankins et al. | |
| 3,964,519 A | 6/1976 | De Baun | |
| 4,127,395 A | 11/1978 | Mckey et al. | |
| 4,144,037 A | 3/1979 | Armond et al. | |
| 4,247,311 A | 1/1981 | Seibert et al. | |
| 4,378,982 A | 4/1983 | Mccombs | |
| 4,449,990 A | 5/1984 | Tedford, Jr. | |
| 4,454,596 A | 6/1984 | Wunsch et al. | |
| 4,561,287 A | 12/1985 | Rowland | |
| 4,575,042 A | 3/1986 | Grimland et al. | |
| 4,648,888 A | 3/1987 | Rowland | |
| 4,750,923 A | 6/1988 | Haruta et al. | |
| 4,826,510 A | 5/1989 | Mccombs | |
| 4,832,711 A | 5/1989 | Christel, Jr. et al. | |
| 4,932,402 A | 6/1990 | Snook et al. | |
| 4,971,609 A | 11/1990 | Pawlos | |
| 5,057,822 A | 10/1991 | Hoffman | |
| 5,099,837 A | 3/1992 | Russel, Sr. et al. | |
| 5,101,656 A | 4/1992 | Miller | |
| 5,144,945 A | 9/1992 | Nishino et al. | |
| 5,258,056 A | 11/1993 | Shirley et al. | |
| 5,294,049 A | 3/1994 | Trunkle et al. | |
| 5,298,226 A | 3/1994 | Nowobilski | |
| 5,340,381 A * | 8/1994 | Vorih .................. C01B 13/0259 |
| | | | 95/21 |
| 5,469,372 A | 11/1995 | Mcbrearty et al. | |
| 5,474,595 A | 12/1995 | Mccombs | |
| 5,538,544 A | 7/1996 | Nowobilski et al. | |
| 5,593,478 A | 1/1997 | Hill et al. | |
| 5,626,131 A | 5/1997 | Chua et al. | |
| 5,680,409 A | 10/1997 | Qin et al. | |
| 5,720,276 A | 2/1998 | Kobatake et al. | |
| 5,779,773 A | 7/1998 | Cam et al. | |
| 5,785,681 A | 7/1998 | Indravudh | |
| 5,906,672 A | 5/1999 | Michaels et al. | |
| 5,917,135 A | 6/1999 | Michaels et al. | |
| 5,931,160 A | 8/1999 | Gilmore et al. | |

| | | | |
|---|---|---|---|
| 5,968,236 A * | 10/1999 | Bassine .............. B01D 53/0446 |
| | | | 96/144 |
| 5,979,440 A * | 11/1999 | Honkonen ......... B01D 53/0454 |
| | | | 128/204.15 |
| 5,983,416 A | 11/1999 | Idland | |
| 5,988,165 A | 11/1999 | Joseph et al. | |
| 6,022,634 A | 2/2000 | Ramunni et al. | |
| 6,051,051 A | 4/2000 | Hees et al. | |
| 6,106,245 A | 8/2000 | Cabuz | |
| 6,110,257 A * | 8/2000 | Tom ...................... F17C 13/025 |
| | | | 96/147 |
| 6,139,426 A | 10/2000 | Koerber | |
| 6,151,586 A | 11/2000 | Brown | |
| 6,152,134 A | 11/2000 | Webber et al. | |
| 6,266,995 B1 | 7/2001 | Scott | |
| 6,279,377 B1 | 8/2001 | Cao | |
| 6,346,139 B1 * | 2/2002 | Czabala .............. A61M 16/101 |
| | | | 96/144 |
| 6,427,690 B1 | 8/2002 | Mccombs et al. | |
| 6,442,433 B1 | 8/2002 | Linberg | |
| 6,472,988 B1 | 10/2002 | Feld et al. | |
| 6,517,610 B1 | 2/2003 | de la Houssaye | |
| 6,520,176 B1 | 2/2003 | Dubois et al. | |
| 6,561,187 B2 | 5/2003 | Schmidt et al. | |
| 6,629,525 B2 | 10/2003 | Hill et al. | |
| 6,651,658 B1 | 11/2003 | Hill et al. | |
| 6,691,702 B2 | 2/2004 | Appel et al. | |
| 6,764,534 B2 | 7/2004 | Mccombs et al. | |
| 6,837,244 B2 | 1/2005 | Yagi et al. | |
| 6,878,186 B2 | 4/2005 | Neary | |
| 6,949,133 B2 * | 9/2005 | McCombs ......... B01D 53/0446 |
| | | | 96/111 |
| 6,962,654 B2 | 11/2005 | Arnaud | |
| 7,036,729 B2 | 5/2006 | Chung | |
| 7,115,104 B2 | 10/2006 | Van Brunt et al. | |
| 7,278,983 B2 | 10/2007 | Ireland et al. | |
| 7,294,170 B2 | 11/2007 | Richey et al. | |
| 7,306,657 B2 | 12/2007 | Yagi et al. | |
| 7,316,733 B1 | 1/2008 | Hedrick et al. | |
| 7,329,304 B2 | 2/2008 | Bliss et al. | |
| 7,331,340 B2 | 2/2008 | Barney | |
| 7,393,382 B2 | 7/2008 | Givens | |
| 7,425,203 B2 | 9/2008 | Van Brunt et al. | |
| 7,431,032 B2 | 10/2008 | Jagger et al. | |
| 7,445,663 B1 | 11/2008 | Hunter et al. | |
| 7,455,717 B2 | 11/2008 | Sprinkle | |
| 7,491,182 B2 | 2/2009 | Van Brunt | |
| 7,505,374 B2 | 3/2009 | Booty, Jr. et al. | |
| 7,552,731 B2 | 6/2009 | Jorczak et al. | |
| 7,604,004 B2 | 10/2009 | Jagger et al. | |
| 7,604,005 B2 | 10/2009 | Jagger et al. | |
| 7,652,571 B2 | 1/2010 | Parkulo et al. | |
| 7,662,638 B2 | 2/2010 | Dadala et al. | |
| 7,686,870 B1 | 3/2010 | Deane et al. | |
| 7,722,698 B2 | 5/2010 | Thompson et al. | |
| 7,722,700 B2 | 5/2010 | Sprinkle | |
| 7,753,996 B1 | 7/2010 | Deane et al. | |
| 7,766,010 B2 | 8/2010 | Jagger et al. | |
| 7,794,522 B2 | 9/2010 | Bliss et al. | |
| 7,826,728 B2 | 11/2010 | Konno et al. | |
| 7,866,315 B2 | 1/2011 | Jagger et al. | |
| 7,875,105 B2 | 1/2011 | Chambers et al. | |
| 7,922,789 B1 | 4/2011 | Deane et al. | |
| 7,931,197 B2 | 4/2011 | Brandt et al. | |
| 8,013,739 B2 | 9/2011 | Parkulo et al. | |
| 8,062,003 B2 | 11/2011 | Goertzen et al. | |
| 8,070,853 B2 | 12/2011 | Sprinkle | |
| 8,092,396 B2 | 1/2012 | Bagha et al. | |
| 8,231,541 B2 | 7/2012 | Colquitt et al. | |
| 8,262,771 B2 | 9/2012 | Seki et al. | |
| 8,366,402 B2 | 2/2013 | St. Michel et al. | |
| 8,366,815 B2 | 2/2013 | Taylor et al. | |
| 8,377,181 B2 | 2/2013 | Taylor et al. | |
| 8,388,745 B1 | 3/2013 | Pelletier et al. | |
| 8,421,465 B2 | 4/2013 | Carter | |
| 8,547,062 B2 | 10/2013 | Carter et al. | |
| 8,568,519 B2 | 10/2013 | Taylor et al. | |
| 8,599,016 B2 | 12/2013 | Parkulo et al. | |
| 8,668,767 B2 | 3/2014 | Sprinkle et al. | |

(56) References Cited

U.S. PATENT DOCUMENTS

| | | | |
|---|---|---|---|
| 8,677,998 B2 | 3/2014 | Yamaura et al. | |
| 8,726,744 B2 | 5/2014 | Alburty et al. | |
| 8,818,824 B2 | 8/2014 | Debusk et al. | |
| 8,876,941 B1 * | 11/2014 | Kornbluh | C01B 13/02 |
| | | | 128/204.21 |
| 8,956,289 B2 | 2/2015 | Kitajima et al. | |
| 9,058,741 B2 | 6/2015 | Steinhauer et al. | |
| 9,061,238 B2 | 6/2015 | Null, Jr. et al. | |
| 9,072,849 B2 | 7/2015 | Steinhauer et al. | |
| 9,132,377 B2 | 9/2015 | Richey et al. | |
| 9,175,577 B2 | 11/2015 | Papamoschou et al. | |
| 9,181,001 B2 | 11/2015 | Molinaro et al. | |
| 9,266,053 B2 | 2/2016 | Shelnutt et al. | |
| 9,317,660 B2 | 4/2016 | Burich et al. | |
| 9,327,090 B2 | 5/2016 | Steinhauer et al. | |
| 9,352,110 B2 | 5/2016 | Steinhauer et al. | |
| 9,364,626 B2 | 6/2016 | Carter et al. | |
| 9,440,179 B2 | 9/2016 | Wilkinson et al. | |
| 9,460,262 B2 | 10/2016 | Kaufman et al. | |
| 9,462,977 B2 | 10/2016 | Horseman | |
| 9,637,280 B2 | 5/2017 | Gotoh et al. | |
| 9,693,734 B2 | 7/2017 | Horseman | |
| 9,714,860 B2 | 7/2017 | Obenchain | |
| 9,763,585 B2 | 9/2017 | Addison et al. | |
| 9,782,557 B2 | 10/2017 | Wilkinson et al. | |
| 9,788,735 B2 | 10/2017 | Al-Ali | |
| 9,808,156 B2 | 11/2017 | Horseman | |
| 9,833,142 B2 | 12/2017 | Horseman | |
| 9,838,508 B2 | 12/2017 | Salem | |
| 9,839,786 B2 | 12/2017 | Rondoni et al. | |
| 9,872,623 B2 | 1/2018 | Al-Ali | |
| 9,872,965 B2 | 1/2018 | Baloa Welzien et al. | |
| 9,956,370 B2 | 5/2018 | Wilkinson et al. | |
| 9,957,125 B2 | 5/2018 | Ray | |
| 9,990,466 B2 | 6/2018 | Debusk et al. | |
| 10,004,435 B2 | 6/2018 | Larvenz et al. | |
| 10,010,696 B2 * | 7/2018 | Sprinkle | A61M 16/105 |
| 10,010,969 B2 | 7/2018 | Reed et al. | |
| 10,037,044 B2 | 7/2018 | Laberge et al. | |
| 10,058,269 B2 | 8/2018 | Lynn | |
| 10,108,785 B2 | 10/2018 | Kamen et al. | |
| 10,139,282 B2 | 11/2018 | Chrostowski | |
| 10,148,912 B1 | 12/2018 | Oliver et al. | |
| 10,179,217 B2 | 1/2019 | Steinhauer et al. | |
| 10,252,037 B2 | 4/2019 | Degen et al. | |
| 10,271,779 B2 | 4/2019 | Addison et al. | |
| 10,349,901 B2 | 7/2019 | Osypka et al. | |
| 10,357,628 B2 | 7/2019 | Jagger et al. | |
| 10,391,019 B2 | 8/2019 | Stryker et al. | |
| 10,426,904 B2 | 10/2019 | Broborg et al. | |
| 10,496,788 B2 | 12/2019 | Amarasingham et al. | |
| 10,521,720 B2 | 12/2019 | Detzler et al. | |
| 10,592,637 B2 | 3/2020 | Velamuri et al. | |
| 10,630,814 B2 | 4/2020 | Barnes et al. | |
| 10,753,598 B2 | 8/2020 | Chien | |
| 10,948,175 B2 | 3/2021 | Chien | |
| 11,915,570 B2 | 2/2024 | Budinger et al. | |
| 2002/0053286 A1 | 5/2002 | Czabala | |
| 2002/0096174 A1 | 7/2002 | Hill et al. | |
| 2003/0068828 A1 | 4/2003 | Dadala et al. | |
| 2003/0180164 A1 | 9/2003 | Bunner et al. | |
| 2003/0215342 A1 | 11/2003 | Higashino et al. | |
| 2003/0231967 A1 | 12/2003 | Najafi et al. | |
| 2004/0079359 A1 | 4/2004 | Aylsworth et al. | |
| 2004/0159323 A1 * | 8/2004 | Schmidt | A61M 16/101 |
| | | | 128/204.23 |
| 2004/0167464 A1 | 8/2004 | Ireland et al. | |
| 2004/0237488 A1 | 12/2004 | Stenersen | |
| 2005/0259088 A1 | 11/2005 | Ogasawara et al. | |
| 2005/0263199 A1 | 12/2005 | Meheen | |
| 2006/0005842 A1 | 1/2006 | Rashad et al. | |
| 2006/0013682 A1 | 1/2006 | Martin et al. | |
| 2006/0025932 A1 | 2/2006 | Dadala et al. | |
| 2006/0086251 A1 | 4/2006 | Sprinkle | |
| 2006/0092768 A1 | 5/2006 | Demas | |
| 2006/0092769 A1 | 5/2006 | Demas | |
| 2006/0174871 A1 | 8/2006 | Jagger et al. | |
| 2006/0174872 A1 | 8/2006 | Jagger et al. | |
| 2006/0219245 A1 | 10/2006 | Holder | |
| 2006/0220881 A1 | 10/2006 | Al-Ali et al. | |
| 2006/0227123 A1 | 10/2006 | Bychkov et al. | |
| 2006/0230768 A1 | 10/2006 | Huber et al. | |
| 2006/0230929 A1 | 10/2006 | Bliss et al. | |
| 2006/0251408 A1 | 11/2006 | Konno et al. | |
| 2007/0032733 A1 | 2/2007 | Burton | |
| 2007/0034590 A1 | 2/2007 | Hidding | |
| 2007/0056584 A1 | 3/2007 | Jagger et al. | |
| 2007/0140869 A1 | 6/2007 | St. Michel et al. | |
| 2007/0144519 A1 | 6/2007 | Henry et al. | |
| 2007/0250017 A1 | 10/2007 | Carred et al. | |
| 2008/0007396 A1 | 1/2008 | Parkulo et al. | |
| 2008/0066616 A1 | 3/2008 | Sprinkle | |
| 2008/0136652 A1 | 6/2008 | Vaisnys et al. | |
| 2008/0165629 A1 | 7/2008 | Billeaudeaux | |
| 2008/0238323 A1 | 10/2008 | Chan et al. | |
| 2008/0246277 A1 | 10/2008 | Gallagher et al. | |
| 2008/0257145 A1 | 10/2008 | Sprinkle et al. | |
| 2008/0262657 A1 | 10/2008 | Howell et al. | |
| 2008/0294348 A1 | 11/2008 | Tanaka et al. | |
| 2009/0065526 A1 | 3/2009 | Sprinkle | |
| 2009/0118632 A1 | 5/2009 | Goepp | |
| 2009/0126736 A1 | 5/2009 | Taylor et al. | |
| 2009/0209839 A1 | 8/2009 | Ochs et al. | |
| 2009/0211438 A1 | 8/2009 | Thompson et al. | |
| 2009/0211448 A1 | 8/2009 | Mcclain | |
| 2009/0216747 A1 | 8/2009 | Li et al. | |
| 2009/0232706 A1 | 9/2009 | Dadala et al. | |
| 2009/0316533 A1 | 12/2009 | Liu | |
| 2010/0024729 A1 | 2/2010 | Cao et al. | |
| 2010/0071698 A1 | 3/2010 | Kiritake | |
| 2010/0095841 A1 | 4/2010 | Naheiri | |
| 2010/0106458 A1 | 4/2010 | Leu et al. | |
| 2010/0114218 A1 | 5/2010 | Heath | |
| 2010/0146426 A1 | 6/2010 | Parkulo et al. | |
| 2010/0214877 A1 | 8/2010 | Turk | |
| 2010/0242734 A1 | 9/2010 | Maeda et al. | |
| 2010/0253505 A1 | 10/2010 | Chou | |
| 2010/0294127 A1 | 11/2010 | Dolensky | |
| 2011/0017216 A1 | 1/2011 | Van Brunt et al. | |
| 2011/0036352 A1 | 2/2011 | Estes et al. | |
| 2011/0046996 A1 | 2/2011 | Foucher et al. | |
| 2011/0056904 A1 | 3/2011 | Rozenberg | |
| 2011/0073107 A1 | 3/2011 | Rodman et al. | |
| 2011/0080348 A1 | 4/2011 | Lin et al. | |
| 2011/0126829 A1 | 6/2011 | Carter et al. | |
| 2011/0128008 A1 | 6/2011 | Carter | |
| 2011/0148773 A1 | 6/2011 | Rudolph | |
| 2011/0148775 A1 | 6/2011 | Rudolph et al. | |
| 2011/0161030 A1 | 6/2011 | Niu et al. | |
| 2011/0211425 A1 | 9/2011 | Liu | |
| 2011/0260850 A1 | 10/2011 | Ringenwald | |
| 2011/0276828 A1 | 11/2011 | Tamaki et al. | |
| 2011/0315140 A1 | 12/2011 | Shuman | |
| 2012/0036461 A1 | 2/2012 | Parkulo et al. | |
| 2012/0122545 A1 | 5/2012 | Watkins et al. | |
| 2012/0321529 A1 | 12/2012 | Guo et al. | |
| 2013/0012788 A1 | 1/2013 | Horseman | |
| 2013/0012789 A1 | 1/2013 | Horseman | |
| 2013/0012790 A1 | 1/2013 | Horseman | |
| 2013/0193100 A1 | 8/2013 | Lamoureux | |
| 2013/0233168 A1 | 9/2013 | Richey et al. | |
| 2013/0264218 A1 | 10/2013 | Vinton et al. | |
| 2013/0269519 A1 | 10/2013 | Taylor et al. | |
| 2013/0297330 A1 | 11/2013 | Kamen et al. | |
| 2013/0333702 A1 | 12/2013 | Baloa Welzien et al. | |
| 2014/0000604 A1 | 1/2014 | Steinhauer et al. | |
| 2014/0000605 A1 | 1/2014 | Steinhauer et al. | |
| 2014/0000607 A1 | 1/2014 | Steinhauer et al. | |
| 2014/0000608 A1 | 1/2014 | Steinhauer et al. | |
| 2014/0000609 A1 | 1/2014 | Steinhauer et al. | |
| 2014/0002246 A1 | 1/2014 | Steinhauer et al. | |
| 2014/0006041 A1 | 1/2014 | Steinhauer et al. | |
| 2014/0006052 A1 | 1/2014 | Steinhauer et al. | |
| 2014/0007405 A1 | 1/2014 | Chambers et al. | |

(56) References Cited

U.S. PATENT DOCUMENTS

| | | |
|---|---|---|
| 2014/0049792 A1 | 2/2014 | Ha |
| 2014/0163335 A1 | 6/2014 | Horseman |
| 2014/0163336 A1 | 6/2014 | Horseman |
| 2014/0163337 A1 | 6/2014 | Horseman |
| 2014/0166003 A1 | 6/2014 | Van Brunt et al. |
| 2014/0188516 A1 | 7/2014 | Kamen et al. |
| 2014/0190348 A1 | 7/2014 | Richey et al. |
| 2014/0343854 A1 | 11/2014 | Wollard |
| 2015/0077245 A1 | 3/2015 | Kaufman et al. |
| 2015/0128800 A1 | 5/2015 | Bliss et al. |
| 2015/0164390 A1 | 6/2015 | Larvenz et al. |
| 2015/0174359 A1 | 6/2015 | Elliott et al. |
| 2015/0213224 A1 | 7/2015 | Amarasingham et al. |
| 2015/0234993 A1 | 8/2015 | Detzler et al. |
| 2015/0238721 A1 | 8/2015 | Rumph et al. |
| 2015/0250960 A1 | 9/2015 | Broberg et al. |
| 2015/0320953 A1 | 11/2015 | Acker et al. |
| 2015/0362929 A1 | 12/2015 | Laberge et al. |
| 2016/0001217 A1 | 1/2016 | Williams et al. |
| 2016/0022971 A1 | 1/2016 | Degen et al. |
| 2016/0034042 A1 | 2/2016 | Joo |
| 2016/0122093 A1 | 5/2016 | Gotoh et al. |
| 2016/0152430 A1 | 6/2016 | Ray |
| 2016/0189345 A1 | 6/2016 | Fujita et al. |
| 2016/0206838 A1 | 7/2016 | Steinhauer et al. |
| 2016/0275261 A1 | 9/2016 | Velamuri et al. |
| 2016/0303388 A1 | 10/2016 | Rondoni et al. |
| 2016/0324425 A1 | 11/2016 | Addison et al. |
| 2016/0367197 A1 | 12/2016 | Addison et al. |
| 2016/0371479 A1 | 12/2016 | Wynen et al. |
| 2016/0375218 A1 | 12/2016 | Sprinkle et al. |
| 2016/0378067 A1 | 12/2016 | Bishop |
| 2017/0000395 A1 | 1/2017 | Addison et al. |
| 2017/0000423 A1 | 1/2017 | Addison et al. |
| 2017/0011131 A1 | 1/2017 | Li et al. |
| 2017/0017767 A1 | 1/2017 | Flower et al. |
| 2017/0053077 A1 | 2/2017 | Osypka et al. |
| 2017/0063456 A1 | 3/2017 | Yamasaki et al. |
| 2017/0080262 A1 | 3/2017 | Freres et al. |
| 2017/0087326 A1* | 3/2017 | Wilkinson ........ A61M 16/0672 |
| 2017/0117444 A1 | 4/2017 | Stoll et al. |
| 2017/0119235 A1 | 5/2017 | Hyde et al. |
| 2017/0122774 A1 | 5/2017 | Quady |
| 2017/0202728 A1 | 7/2017 | Stryker et al. |
| 2017/0221414 A1 | 8/2017 | Endo |
| 2017/0224231 A1 | 8/2017 | Ai-Ali |
| 2017/0224233 A1 | 8/2017 | Al-Ali |
| 2017/0291708 A1 | 10/2017 | Buenting et al. |
| 2018/0014791 A1 | 1/2018 | Montgomery et al. |
| 2018/0156667 A1 | 6/2018 | Chrostowski |
| 2018/0192965 A1 | 7/2018 | Rose et al. |
| 2018/0271421 A1 | 9/2018 | Larvenz et al. |
| 2018/0279475 A1 | 9/2018 | Kloth et al. |
| 2018/0289992 A1 | 10/2018 | Peake |
| 2018/0314416 A1 | 11/2018 | Powderly et al. |
| 2018/0353718 A1* | 12/2018 | Gale ..................... G16H 20/40 |
| 2018/0369532 A1 | 12/2018 | Nebrigic |
| 2019/0065973 A1 | 2/2019 | Elwakeel |
| 2019/0068760 A1 | 2/2019 | Barnes et al. |
| 2019/0134340 A1 | 5/2019 | Nebrigac |
| 2019/0143056 A1 | 5/2019 | Steinhauer et al. |
| 2019/0200577 A1 | 7/2019 | Kath |
| 2019/0295718 A1 | 9/2019 | Lawhorn |
| 2019/0341793 A1 | 11/2019 | Chien |
| 2019/0374139 A1 | 12/2019 | Kiani et al. |
| 2020/0013501 A1 | 1/2020 | Page et al. |
| 2020/0016605 A1 | 1/2020 | Nebrigac |
| 2020/0035348 A1 | 1/2020 | Sartor et al. |
| 2020/0060545 A1 | 2/2020 | Maher et al. |
| 2020/0064011 A1 | 2/2020 | Nakano |
| 2020/0081856 A1 | 3/2020 | Kojima |
| 2020/0146442 A1 | 5/2020 | Rutzke |
| 2020/0193806 A1 | 6/2020 | Finke et al. |
| 2020/0264031 A1 | 8/2020 | Lease et al. |
| 2021/0038855 A1* | 2/2021 | Oddo ....................... F04F 5/16 |

| | | |
|---|---|---|
| 2021/0069360 A1 | 3/2021 | Shane et al. |
| 2021/0249010 A1 | 8/2021 | Tayshete et al. |
| 2021/0252317 A1 | 8/2021 | Peake |
| 2021/0366320 A1 | 11/2021 | Wang et al. |
| 2022/0134035 A1* | 5/2022 | Miaralipour ......... B01D 53/047 |
| | | 128/205.27 |
| 2022/0305428 A1 | 9/2022 | Yehya et al. |

FOREIGN PATENT DOCUMENTS

| | | |
|---|---|---|
| AU | 748829 B2 | 6/2002 |
| AU | 200072387 A | 6/2002 |
| AU | 2008240038 A1 | 10/2008 |
| AU | 2010282150 A1 | 7/2012 |
| AU | 2012279039 A1 | 1/2014 |
| AU | 2012279044 A1 | 1/2014 |
| AU | 2012279110 A1 | 1/2014 |
| AU | 2013364131 A1 | 7/2015 |
| AU | 2013364131 A8 | 9/2015 |
| AU | 2013364131 A2 | 10/2015 |
| AU | 2014357428 B2 | 5/2019 |
| AU | 2013364131 B2 | 7/2019 |
| AU | 2018258679 A1 | 11/2019 |
| AU | 2018295533 A1 | 1/2020 |
| BR | PI1515024 A2 | 7/2017 |
| CA | 2310667 A1 | 6/1999 |
| CA | 2379697 A1 | 2/2001 |
| CA | 2438457 A1 | 2/2004 |
| CA | 2772539 A1 | 6/2004 |
| CA | 2683367 A1 | 10/2008 |
| CA | 2506292 C | 5/2012 |
| CA | 2839287 A1 | 1/2013 |
| CA | 2840969 A1 | 1/2013 |
| CA | 2840975 A1 | 1/2013 |
| CA | 2840984 A1 | 1/2013 |
| CA | 3016496 A1 | 1/2013 |
| CA | 2310667 C | 7/2013 |
| CA | 2772539 C | 4/2014 |
| CA | 2896086 A1 | 6/2014 |
| CA | 2933599 A1 | 6/2015 |
| CA | 2945137 A1 | 10/2015 |
| CA | 2982855 A1 | 11/2016 |
| CA | 2840979 C | 7/2018 |
| CA | 3050643 A1 | 7/2018 |
| CA | 3059209 A1 | 11/2018 |
| CA | 3069278 A1 | 1/2019 |
| CA | 2933599 C | 12/2019 |
| CA | 3016496 C | 1/2020 |
| CA | 3189534 A1 | 1/2022 |
| CA | 3189535 A1 | 1/2022 |
| CA | 3189540 A1 | 1/2022 |
| CA | 3189542 A1 | 1/2022 |
| CA | 3189544 A1 | 1/2022 |
| CA | 3189568 A1 | 1/2022 |
| CA | 3189573 A1 | 1/2022 |
| CN | 87102164 A | 11/1987 |
| CN | 2585215 Y | 11/2003 |
| CN | 1610516 A | 4/2005 |
| CN | 1697681 A | 11/2005 |
| CN | 1697682 A | 11/2005 |
| CN | 1780655 A | 5/2006 |
| CN | 2839861 Y | 11/2006 |
| CN | 101506868 A | 8/2009 |
| CN | 101520690 A | 9/2009 |
| CN | 101681455 A | 3/2010 |
| CN | 101687134 A | 3/2010 |
| CN | 101873824 A | 10/2010 |
| CN | 1780655 B | 12/2010 |
| CN | 101520690 B | 7/2011 |
| CN | 101141567 B | 12/2012 |
| CN | 101687134 B | 12/2013 |
| CN | 103448727 A | 12/2013 |
| CN | 103534664 A | 1/2014 |
| CN | 101543047 B | 2/2014 |
| CN | 103764021 A | 4/2014 |
| CN | 103781405 A | 5/2014 |
| CN | 103781409 A | 5/2014 |
| CN | 104235038 A | 12/2014 |
| CN | 204226229 U | 3/2015 |

(56)                References Cited

FOREIGN PATENT DOCUMENTS

| | | | |
|---|---|---|---|
| CN | 104951225 | A | 9/2015 |
| CN | 104969227 | A | 10/2015 |
| CN | 105269352 | A | 1/2016 |
| CN | 105351296 | A | 2/2016 |
| CN | 205237581 | U | 5/2016 |
| CN | 205302544 | U | 6/2016 |
| CN | 205344448 | U | 6/2016 |
| CN | 205578301 | U | 9/2016 |
| CN | 205578306 | U | 9/2016 |
| CN | 205644217 | U | 10/2016 |
| CN | 106075696 | A | 11/2016 |
| CN | 106102571 | A | 11/2016 |
| CN | 106455927 | A | 2/2017 |
| CN | 103477340 | B | 3/2017 |
| CN | 106574784 | A | 4/2017 |
| CN | 106793238 | A | 5/2017 |
| CN | 106887110 | A | 6/2017 |
| CN | 106913326 | A | 7/2017 |
| CN | 106931478 | A | 7/2017 |
| CN | 206459246 | U | 9/2017 |
| CN | 206655848 | U | 11/2017 |
| CN | 108348148 | A | 7/2018 |
| CN | 108430559 | A | 8/2018 |
| CN | 105373219 | B | 9/2018 |
| CN | 109171755 | A | 1/2019 |
| CN | 110292696 | A | 10/2019 |
| CN | 110431509 | A | 11/2019 |
| CN | 110604580 | A | 12/2019 |
| CN | 107430497 | B | 3/2020 |
| CN | 111792030 | A | 10/2020 |
| DE | 573822 | C | 4/1933 |
| DE | 3723019 | A1 | 1/1989 |
| DE | 29605889 | U1 | 8/1996 |
| DE | 19936893 | A1 | 2/2001 |
| DE | 10037227 | A1 | 2/2002 |
| DE | 19936893 | C2 | 8/2002 |
| DE | 102005042268 | A1 | 5/2006 |
| DE | 102007021564 | A1 | 11/2008 |
| DE | 202006020670 | U1 | 7/2009 |
| DE | 102008016768 | A1 | 10/2009 |
| DE | 102008030790 | A1 | 12/2009 |
| DE | 102014103377 | A1 | 9/2014 |
| DE | 102014103397 | A1 | 9/2014 |
| DE | 102016116761 | A1 | 3/2017 |
| DE | 102017204049 | B3 | 5/2018 |
| DE | 102018115858 | A1 | 1/2020 |
| EP | 420620 | A2 | 4/1991 |
| EP | 885645 | A2 | 12/1998 |
| EP | 1032906 | A1 | 9/2000 |
| EP | 1157731 | A1 | 11/2001 |
| EP | 885645 | B1 | 1/2005 |
| EP | 1661596 | A2 | 5/2006 |
| EP | 1707928 | A1 | 10/2006 |
| EP | 1895892 | A1 | 3/2008 |
| EP | 1340071 | B1 | 3/2009 |
| EP | 2136682 | A1 | 12/2009 |
| EP | 2138060 | A2 | 12/2009 |
| EP | 2197530 | A2 | 6/2010 |
| EP | 2266093 | A2 | 12/2010 |
| EP | 2058787 | B1 | 12/2013 |
| EP | 2729052 | A1 | 5/2014 |
| EP | 2729054 | A1 | 5/2014 |
| EP | 2729056 | A1 | 5/2014 |
| EP | 2751751 | A1 | 7/2014 |
| EP | 2773410 | A1 | 9/2014 |
| EP | 2861139 | A1 | 4/2015 |
| EP | 2895224 | A1 | 7/2015 |
| EP | 2936362 | A2 | 10/2015 |
| EP | 1636076 | B1 | 12/2015 |
| EP | 2613838 | B1 | 3/2016 |
| EP | 2138060 | B1 | 6/2016 |
| EP | 3069279 | A1 | 9/2016 |
| EP | 3082977 | A2 | 10/2016 |
| EP | 3117355 | A1 | 1/2017 |
| EP | 3129949 | A2 | 2/2017 |
| EP | 1850917 | B1 | 6/2017 |
| EP | 3282382 | A1 | 2/2018 |
| EP | 3283165 | A1 | 2/2018 |
| EP | 3286910 | A1 | 2/2018 |
| EP | 3294120 | A1 | 3/2018 |
| EP | 3316769 | A1 | 5/2018 |
| EP | 3316770 | A1 | 5/2018 |
| EP | 2729051 | B1 | 6/2018 |
| EP | 3372910 | A1 | 9/2018 |
| EP | 2058162 | B1 | 1/2019 |
| EP | 2936362 | B1 | 3/2019 |
| EP | 3578220 | A1 | 12/2019 |
| EP | 3614946 | A1 | 3/2020 |
| EP | 3616040 | A1 | 3/2020 |
| EP | 3627261 | A1 | 3/2020 |
| EP | 3634538 | A1 | 4/2020 |
| EP | 3638557 | A1 | 4/2020 |
| FR | 2865655 | A1 | 8/2005 |
| FR | 2865655 | B1 | 4/2006 |
| GB | 1270296 | A | 4/1972 |
| GB | 1375908 | A | 12/1974 |
| IN | 201202311 | P4 | 5/2013 |
| IN | 201504225 | P4 | 7/2016 |
| IN | 201647029095 | A | 10/2016 |
| IN | 201721043516 | A | 12/2017 |
| IN | 379045 | A1 | 10/2021 |
| IN | 499375 | A1 | 1/2024 |
| IN | 531840 | A1 | 4/2024 |
| JP | 63134026 | A | 6/1988 |
| JP | 693850 | A | 4/1994 |
| JP | 10066820 | A | 3/1998 |
| JP | 10104190 | A | 4/1998 |
| JP | 2001095920 | A | 4/2001 |
| JP | 2002239330 | A | 8/2002 |
| JP | 2002297807 | A | 10/2002 |
| JP | 3348956 | B2 | 11/2002 |
| JP | 2003024269 | A | 1/2003 |
| JP | 2004258828 | A | 9/2004 |
| JP | 2005098571 | A | 4/2005 |
| JP | 2005245735 | A | 9/2005 |
| JP | 2006153337 | A | 6/2006 |
| JP | 2007508572 | A | 4/2007 |
| JP | 2007170410 | A | 7/2007 |
| JP | 2008011933 | A | 1/2008 |
| JP | 2008113861 | A | 5/2008 |
| JP | 2008167917 | A | 7/2008 |
| JP | 2008531218 | A | 8/2008 |
| JP | 2008209094 | A | 9/2008 |
| JP | 2008276275 | A | 11/2008 |
| JP | 2010502423 | A | 1/2010 |
| JP | 4469972 | B2 | 6/2010 |
| JP | 2010119762 | A | 6/2010 |
| JP | 2010287576 | A | 12/2010 |
| JP | 2011075223 | A | 4/2011 |
| JP | 2011106373 | A | 6/2011 |
| JP | 2011520170 | A | 7/2011 |
| JP | 2012157812 | A | 8/2012 |
| JP | 5020358 | B2 | 9/2012 |
| JP | 5250037 | B2 | 7/2013 |
| JP | 5275955 | B2 | 8/2013 |
| JP | 2013218725 | A | 10/2013 |
| JP | 2014064771 | A | 4/2014 |
| JP | 2014523038 | A | 9/2014 |
| JP | 2014523039 | A | 9/2014 |
| JP | 2014524797 | A | 9/2014 |
| JP | 2014225236 | A | 12/2014 |
| JP | 2015007083 | A | 1/2015 |
| JP | 5711389 | B2 | 4/2015 |
| JP | 2015531310 | A | 11/2015 |
| JP | 2015217211 | A | 12/2015 |
| JP | 2016033154 | A | 3/2016 |
| JP | 2016509284 | A | 3/2016 |
| JP | 2016197422 | A | 11/2016 |
| JP | 2017503571 | A | 2/2017 |
| JP | 2017508532 | A | 3/2017 |
| JP | 06144238 | B2 | 6/2017 |
| JP | 2017105839 | A | 6/2017 |
| JP | 2017130833 | A | 7/2017 |
| JP | 2017138567 | A | 8/2017 |

(56)　　　　　References Cited

FOREIGN PATENT DOCUMENTS

| JP | 2017143589 A | 8/2017 |
| JP | 2017146065 A | 8/2017 |
| JP | 06203634 B2 | 9/2017 |
| JP | 06252607 B2 | 12/2017 |
| JP | 6307238 B2 | 4/2018 |
| JP | 2018511440 A | 4/2018 |
| JP | 2018122119 A | 8/2018 |
| JP | 2018531152 A | 10/2018 |
| JP | 2019500927 A | 1/2019 |
| JP | 2019082290 A | 5/2019 |
| JP | 2019207684 A | 12/2019 |
| JP | 2020011074 A | 1/2020 |
| JP | 6709479 B1 | 6/2020 |
| JP | 2023502570 A | 1/2023 |
| JP | 7580153 B2 | 11/2024 |
| KR | 2009069335 A | 6/2009 |
| KR | 2014070553 A | 6/2014 |
| KR | 2014114422 A | 9/2014 |
| KR | 1020150117092 A | 10/2015 |
| KR | 1816443 B1 | 1/2018 |
| KR | 2018009326 A | 1/2018 |
| KR | 2072394 B1 | 2/2020 |
| KR | 2020031433 A | 3/2020 |
| KR | 2103631 B1 | 4/2020 |
| KR | 2020054445 A | 5/2020 |
| MX | 2010005090 A | 5/2010 |
| MX | 2014007304 A | 7/2014 |
| MX | 2015004842 A | 7/2015 |
| MX | 355476 B | 4/2018 |
| NO | 178100 B | 10/1995 |
| RU | 2015143725 A | 4/2017 |
| WO | 9707439 A1 | 2/1997 |
| WO | 9807930 A1 | 2/1998 |
| WO | 9856488 A1 | 12/1998 |
| WO | 9857165 A1 | 12/1998 |
| WO | 9927483 A1 | 6/1999 |
| WO | 0108752 A1 | 2/2001 |
| WO | 2004009161 A1 | 1/2004 |
| WO | 2005029452 A2 | 3/2005 |
| WO | 2005071372 A1 | 8/2005 |
| WO | 2006086415 A2 | 8/2006 |
| WO | 2006086472 A2 | 8/2006 |
| WO | 2006086522 A2 | 8/2006 |
| WO | 2006092635 A1 | 9/2006 |
| WO | 2006118654 A1 | 11/2006 |
| WO | 2007072385 A2 | 6/2007 |
| WO | 2007095266 A2 | 8/2007 |
| WO | 2008036159 A1 | 3/2008 |
| WO | 2008128250 A1 | 10/2008 |
| WO | 2008131338 A1 | 10/2008 |
| WO | 2009022320 A2 | 2/2009 |
| WO | 2009032540 A2 | 3/2009 |
| WO | 2009052704 A1 | 4/2009 |
| WO | 2009105541 A1 | 8/2009 |
| WO | 2009114249 A2 | 9/2009 |
| WO | 2009148646 A2 | 12/2009 |
| WO | 2010082322 A1 | 7/2010 |
| WO | 2011088539 A1 | 7/2011 |
| WO | 2011017778 A9 | 11/2012 |
| WO | 2012174420 A2 | 12/2012 |
| WO | 2013006615 A1 | 1/2013 |
| WO | 2013006627 A1 | 1/2013 |
| WO | 2013006632 A1 | 1/2013 |
| WO | 2013067223 A1 | 5/2013 |
| WO | 2013134645 A1 | 9/2013 |
| WO | 2013188013 A1 | 12/2013 |
| WO | 2014005106 A1 | 1/2014 |
| WO | 2014041104 A1 | 3/2014 |
| WO | 2014060726 A1 | 4/2014 |
| WO | 2014071145 A1 | 5/2014 |
| WO | 2014100687 A2 | 6/2014 |
| WO | 2014101824 A1 | 7/2014 |
| WO | 2014132051 A2 | 9/2014 |
| WO | 2015073459 A1 | 5/2015 |
| WO | 2015095532 A2 | 6/2015 |
| WO | 2015136502 A1 | 9/2015 |
| WO | 2015157575 A2 | 10/2015 |
| WO | 2016105552 A1 | 6/2016 |
| WO | 2016168119 A1 | 10/2016 |
| WO | 2016172469 A1 | 10/2016 |
| WO | 2016182853 A1 | 11/2016 |
| WO | 2017004068 A1 | 1/2017 |
| WO | 2017004069 A1 | 1/2017 |
| WO | 2017029396 A1 | 2/2017 |
| WO | 2017101747 A1 | 6/2017 |
| WO | 2017106636 A1 | 6/2017 |
| WO | 2017106644 A1 | 6/2017 |
| WO | 2017126392 A1 | 7/2017 |
| WO | 2017141774 A1 | 8/2017 |
| WO | 2017218295 A1 | 12/2017 |
| WO | 2018016852 A1 | 1/2018 |
| WO | 2018044959 A1 | 3/2018 |
| WO | 2018200865 A1 | 11/2018 |
| WO | 2018201067 A1 | 11/2018 |
| WO | 2018209112 A1 | 11/2018 |
| WO | 2019008529 A1 | 1/2019 |
| WO | 2019202390 A1 | 10/2019 |
| WO | 2019236759 A1 | 12/2019 |
| WO | 2020023186 A1 | 1/2020 |
| WO | 2020037375 A1 | 2/2020 |
| WO | 2020041785 A1 | 2/2020 |
| WO | 2020042639 A1 | 3/2020 |
| WO | 2020086528 A1 | 4/2020 |
| WO | WO-2021056065 A1 * | 4/2021 | .......... A61M 16/024 |
| WO | WO-2021194416 A1 * | 9/2021 | ........... A61B 5/0816 |
| WO | WO-2021194426 A1 * | 9/2021 | .......... A61M 16/024 |
| WO | WO-2022005388 A1 * | 1/2022 | ........ A61M 16/0063 |

OTHER PUBLICATIONS

U.S. Appl. No. 62/904,858 (hereinafter: Navarro et al.) ; 98 pages; filed Sep. 24, 2019; entire document printed from the Internet on Nov. 2, 2023 (Year: 2019).*

Invacare Perfecto2 Tm V Oxygen Concentrator Brochure, 2009, 2 pages.

Invacare SOLO2 TM Transportable Oxygen Concentrator User Manual, 2010, 52 pages.

Invacare XPO2 Portable TM Portable Oxygen Concentrator Brochure, 2010, 4 pages.

Invacare Platinum 10L Oxygen Concentrator IRC10LX02 en HomeFill® System Compatible User Manual, 2016, 36 pages.

Invacare Platinum Mobile POC1-100B, POC1-100C en Oxygen Concentrator User Manual, 2018, 160 pages.

Chinh et al. "Simulation and Experimental Study of a Single Fixed-Bed Model of Nitrogen Gas Generator Working by Pressure Swing Adsorption" , MDPI, Processes 2019, retrieved on 22.09. 2021, retrieved from <URL: https://www. mdpl.com/2227-9717/7/ 10/654/, entire document.

Invacare Platinum 10 Oxygen Concentrator Brochure, 2019, 2 pages.

International Search Report and Written Opinion from PCT/US2021/ 041712 dated Dec. 16, 2021.

International Search Report and Written Opinion from PCT/US2021/ 041718 dated Nov. 4, 2021.

International Search Report and Written Opinion from PCT/US2021/ 041719 dated Oct. 27, 2021.

International Search Report and Written Opinion from PCT/US21/ 41710 dated Nov. 15, 2021, 16 pages.

International Search Report and Written Opinion from PCT/US21/ 41711 dated Oct. 21, 2021, 13 pages.

International Search Report and Written Opinion from PCT/US21/ 41714 dated Nov. 15, 2021, 13 pages.

International Search Report and Written Opinion from PCT/US21/ 41717 dated Oct. 21, 2021.

Notice of Allowance from U.S. Appl. No. 17/376,253 dated Nov. 24, 2023.

Notice of Allowance from U.S. Appl. No. 17/376,278 dated Oct. 23, 2023.

Office Action for Japanese Patent Application No. 2023-502663 dated Dec. 27, 2023, 11 pages.

(56)        References Cited

OTHER PUBLICATIONS

Office Action for Japanese Patent Application No. 2023-502664 dated Sep. 5, 2023, 5 pages.
Office Action for Japanese Patent Application No. 2023-502667 mailed Aug. 28, 2023.
Office Action for Japanese Patent Application No. 2023-502670 dated Apr. 2, 2024, 10 pages.
Office Action for Japanese Patent Application No. 2023-502671 dated Jul. 29, 2024, 11 pages.
Britannica, the Editors of Encyclopaedia, "Newton's laws of motion", Encyclopedia Britannica, Mar. 28, 2024, 2 pgs., https://www.britannica.com/science/Newtons-laws-of-motion (Year 2024).
Notice of Allowance from U.S. Appl. No. 17/376,202 dated Apr. 24, 2024, 9 pages.
Notice of Allowance from U.S. Appl. No. 17/376,202 dated Aug. 9, 2024, 5 pages.
Notice of Allowance from U.S. Appl. No. 17/376,241 dated Oct. 30, 2024, 6 pages.
Notice of Allowance from U.S. Appl. No. 17/376,266 dated Aug. 14, 2024, 8 pages.
Notice of Allowance from U.S. Appl. No. 17/376,266 dated Jul. 25, 2024.
Office Action for Canadian Patent Application No. 3,189,544 dated Jun. 4, 2024, 4 pages.
Office Action for European Patent Application No. 21842977.7 dated Oct. 25, 2024, 11 pages.
Office Action for Japanese Patent Application No. 2024-007939 dated Sep. 19, 2024, 7 pages.
Office action from CA Application No. 3,189,534 dated May 24, 2024.
Office action from Canadian Application No. 3, 189,535 dated Apr. 29, 2024.
Office action from Canadian Application No. 3, 189,540 dated Apr. 30, 2024.
Office action from Canadian Application No. 3, 189,542 dated Aug. 2, 2024.
Notice of Allowance from U.S. Appl. No. 17/376,241 dated Mar. 4, 2025, 6 pages.
Ridl, "Audible Alerts and Visible Signals for the Inogen One GS", Inogen One GS blog, 30.10.2019. (12 pages.
Office Action from U.S. Appl. No. 17/376,202 dated Jun. 7, 2023.
Office Action from U.S. Appl. No. 17/376,241 dated Dec. 8, 2023.
Office Action from U.S. Appl. No. 17/376,266 dated Oct. 12, 2023.
Office Action from U.S. Appl. No. 17/376,278 dated Aug. 23, 2023.
Office action from Japanese Application No. 2023-502665 dated Mar. 11, 2024.
Office action from Japanese Application No. 2023-502666 dated May 23, 2024.
Office action from Japanese Application No. 2023-502670 dated Aug. 7, 2024.

Office action from Japanese Application No. 2023-502670 dated Mar. 29, 2024.
Office action from Japanese Application No. 2023-502671 dated Jan. 17, 2025, 10 pages.
Office action from Japanese Application No. 2023-502671 dated Mar. 13, 2024.
Office Action from U.S. Appl. No. 17/376,197 dated May 8, 2024.
Office Action from U.S. Appl. No. 17/376,197 dated Nov. 1, 2024, 75 pages.
Office Action from U.S. Appl. No. 17/376,202 dated Jan. 3, 2024.
Office Action from U.S. Appl. No. 17/376,266 dated Apr. 5, 2024.
Office action from Canadian Application No. 3, 189,573 dated May 24, 2024.
Office action from Canadian Application No. 3189568 dated Jun. 4, 2024.
Office action from U.S. Appl. No. 17/376,205 dated Aug. 9, 2024.
Office action from U.S. Appl. No. 17/376,241 dated Jun. 7, 2024.
Restriction Requirement from U.S. Appl. No. 17/376,205 dated Mar. 7, 2024, 8 pages.
Restriction Requirement from U.S. Appl. No. 17/376,205 dated May 23, 2024, 6 pages.
Search Report from European Application No. 21842676.5 dated Jul. 8, 2024.
Search Report from European Application No. 21843492.6 dated Jul. 10, 2024.
Search Report from European Application No. 21843561.8 dated Jun. 27, 2024.
Office Action from Canadian Application No. 3, 189,535 dated May 29, 2025, 4 pages.
Office Action from Canadian Application No. 3, 189,568 dated Jun. 12, 2025, 5 pages.
Office Action from Chinese Application No. 202180062668.7 dated Mar. 31, 2025, 4 pages.
Office Action from Chinese Application No. 202180063238.7 dated May 30, 2025, 24 pages.
Office Action from U.S. Appl. No. 17/376,205 dated Jan. 24, 2025, 31 pages.
Office Action from U.S. Appl. No. 17/376,205 dated May 1, 2025, 20 pages.
Office Action from U.S. Appl. No. 18/418,447 dated May 6, 2025, 12 pages.
Offiec Action from Chinese Application No. 202180062666.8 dated Jun. 7, 2025, 46 pages.
Search Report from European Application No. 21841900.0 dated Apr. 2, 2025, 9 pages.
Search Report from European Application No. 21842403.4 dated Apr. 7, 2025.
Search Report from European Application No. 21842520.5 dated Apr. 2, 2025, 8 pages.

* cited by examiner

400

402 — Determine Initial Values

404 — Establish Baseline Based on Altitude

406 — Change In Altitude?

Yes

No

408 — Collect Data

410 — Has Data Analysis Threshold Been Met?

No

Yes

412 — Perform Analysis and Calculate Time to Failure

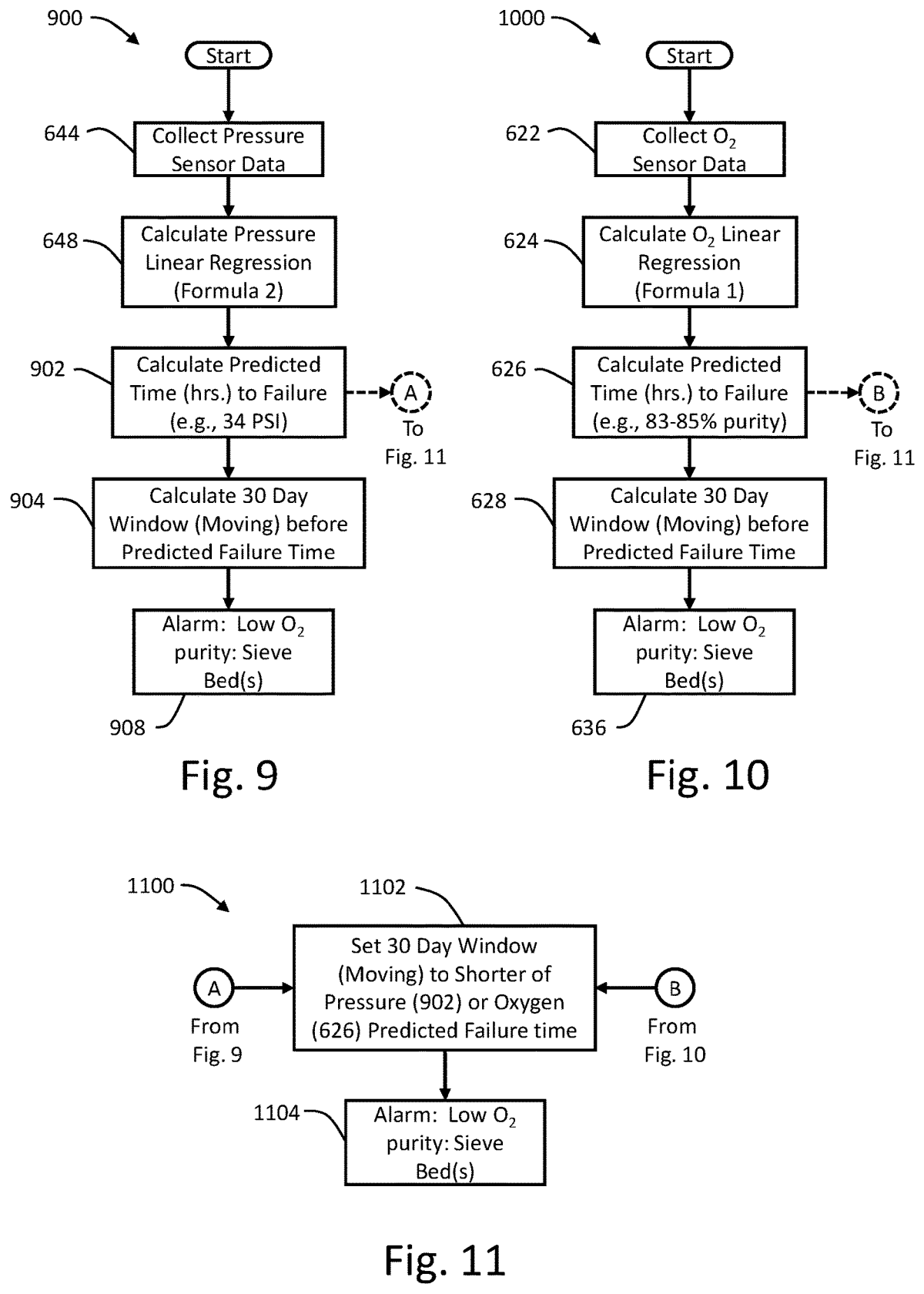

900

Start

644 — Collect Pressure Sensor Data

648 — Calculate Pressure Linear Regression (Formula 2)

902 — Calculate Predicted Time (hrs.) to Failure (e.g., 34 PSI) ⇢ (A) To Fig. 11

904 — Calculate 30 Day Window (Moving) before Predicted Failure Time

Alarm: Low O₂ purity: Sieve Bed(s)

Start

622 — Collect O₂ Sensor Data

624 — Calculate O₂ Linear Regression (Formula 1)

626 — Calculate Predicted Time (hrs.) to Failure (e.g., 83-85% purity) ⇢ (B) To Fig. 11

628 — Calculate 30 Day Window (Moving) before Predicted Failure Time

Alarm: Low O₂ purity: Sieve Bed(s)

(A) From Fig. 9 → Set 30 Day Window (Moving) to Shorter of Pressure (902) or Oxygen (626) Predicted Failure time ← (B) From Fig. 10

1104 — Alarm: Low O₂ purity: Sieve Bed(s)

Fig. 11

SYSTEM AND METHOD FOR CONCENTRATING GAS

CROSS-REFERENCES TO RELATED APPLICATIONS

This application claims priority to U.S. patent application Ser. No. 17/376,253 titled "System and Method for Concentrating Gas," filed Jul. 15, 2021, and to U.S. Prov. Pat. App. Ser. No. 63/052,869 titled "System and Method for Concentrating Gas" filed on Jul. 16, 2020.

This application incorporates by reference the following patent applications: U.S. Prov. Pat. App. Ser. No. 63/052,694 titled "System and Method for Concentrating Gas"; U.S. Prov. Pat. App. Ser. No. 63/052,700 titled "System and Method for Concentrating Gas"; U.S. Prov. Pat. App. Ser. No. 63/052,869 titled "System and Method for Concentrating Gas"; U.S. Prov. Pat. App. Ser. No. 63/052,533 titled "System and Method for Concentrating Gas"; and U.S. Prov. Pat. App. Ser. No. 63/052,647 titled "System and Method for Managing Medical Devices", all filed on Jul. 16, 2020.

BACKGROUND

Various applications exist for the separation of gaseous mixtures. For example, the separation of nitrogen from atmospheric air can provide a highly concentrated source of oxygen. These various applications include the provision of elevated concentrations of oxygen for medical patients and flight personnel. Hence, it is desirable to provide systems that separate gaseous mixtures to provide a concentrated product gas, such as a breathing gas with a concentration of oxygen.

Several existing product gas or oxygen concentrating systems and methods, for example, are disclosed in U.S. Pat. Nos. 4,449,990, 5,906,672, 5,917,135, 5,988,165, 7,294,170, 7,455,717, 7,722,700, 7,875,105, 8,062,003, 8,070,853, 8,668,767, 9,132,377, 9,266,053, and 10,010,696 which are commonly assigned to Invacare Corporation of Elyria, Ohio and fully incorporated herein by reference.

Such systems are known to be either stationary, transportable, or portable. Stationary systems are intended to remain in one location such as, for example, a user's bedroom or living room. Transportable systems are intended to be moved from location to location and often include wheels or other mechanisms to facilitate movement. Portable systems are intended to be carried with the user such as, for example, via a shoulder strap or similar accessory.

Failure of one or more components of these systems results in the system needing to be either repaired or replaced without much advance notice. If the system cannot be quickly repaired or replaced, a suitable alternative must be found for the user. While such systems have hardware and software configured to monitor various sensors, this monitoring has been associated the gas concentrating process and limited diagnostics. Hence, it is desired to provide systems and methods with improved data/diagnostic analysis and control capabilities including, but not limited to, time to component failure.

SUMMARY

Gas concentrating systems and methods are provided. The systems and methods may, for example, calculate a time to failure for one or more system components, generate alarms to warn a user of pending component failure, modify system settings to improve functionality in differing environmental conditions, modify system operation to conserve energy, and/or determine optimal setting configurations based on sensor feedback. Component specific alarms can help with diagnostics at the medical device provider level, increase the efficiency of service and repair, and save costs by reducing the probability that components are wrongly replaced.

In one embodiment, systems and methods for calculating a time to failure for at least one component of a gas concentrating system is provided. The systems and methods include using operating pressure and/or oxygen concentration time slope linear regression to determine an estimated time to failure. In other embodiments, this determination can be made periodically to update or refresh the estimated time to failure. Further, component failing can be identified by, for example, the pressure and/or oxygen the slope trend (positive or negative) and the decay/linear regression in oxygen purity. Based on this identification, warnings, alarms, and the like, can be generated to alert users and service personal as to which components are at issue.

In another embodiment, the systems and methods create baseline readings based on altitude values. This comprises determining initial values related to operation of the gas concentrating system, including at least an average oxygen value, an average pressure value, and an altitude value. In one embodiment, the systems and methods further comprise establishing a baseline of values for a given altitude value and determining if a change in altitude has occurred. If a change in altitude is determined, the systems and methods establish a second baseline of values for the measured altitude. If no change in altitude is determined, the systems and methods proceed to collect data based on the values related to the operation of the gas concentrating system. In another embodiment, the systems and methods further comprise determining if a data analysis threshold has been met, and if so, performing analysis and calculating an estimated time to component failure.

In another embodiment, the systems and methods may further comprise determining a maintenance window, collecting data during the maintenance window, determining if a data analysis threshold has been met, performing a second analysis and calculating an estimated time to component failure, diagnosing a failure component, and generating an alert based on the diagnosed failure component.

It is thus an object of the inventions to determine time to failure or health of one or more components of a gas concentrating system.

It is another object to provide one or more component failure alarms or warnings based on a time to failure or heath analysis of at least one component.

It is another object to provide one or more component failure or health alarms or warnings prior to a component failure.

It is another object to provide a system and method for concentrating gas that performs a time to failure or heath analysis of at least one component of the system and uses that information to inform the user that service is presently required or needed in the near future.

It is another object to provide a system and method for concentrating gas that performs a time to failure or health analysis of at least one component of the system and uses that information to inform service or repair personnel that one or more components require service or repair presently or in the near future.

It is another object to provide a system and method for concentrating gas that performs a time to failure or health analysis of at least one component of the system and uses that information to modify the performance of the system and method to extend the useful life of the component or system.

These and other objects will be apparent from the drawings and the description of the inventions provided herein above and below.

BRIEF DESCRIPTION OF THE DRAWINGS

In the accompanying drawings which are incorporated in and constitute a part of the specification, embodiments of the inventions are illustrated, which, together with a general description of the inventions given above, and the detailed description given below, serve to example the principles of the inventions.

FIG. 9 illustrates another embodiment of a method and logic for diagnosing the failure, predicted failure and/or health of one or more components in a gas concentrating system.

FIG. 10 illustrates yet another embodiment of a method and logic for diagnosing the failure, predicted failure and/or health of one or more components in a gas concentrating system.

FIG. 11 illustrates a further embodiment of a method and logic for diagnosing the failure, predicted failure and/or health of one or more components in a gas concentrating system.

DESCRIPTION

Figure 1:
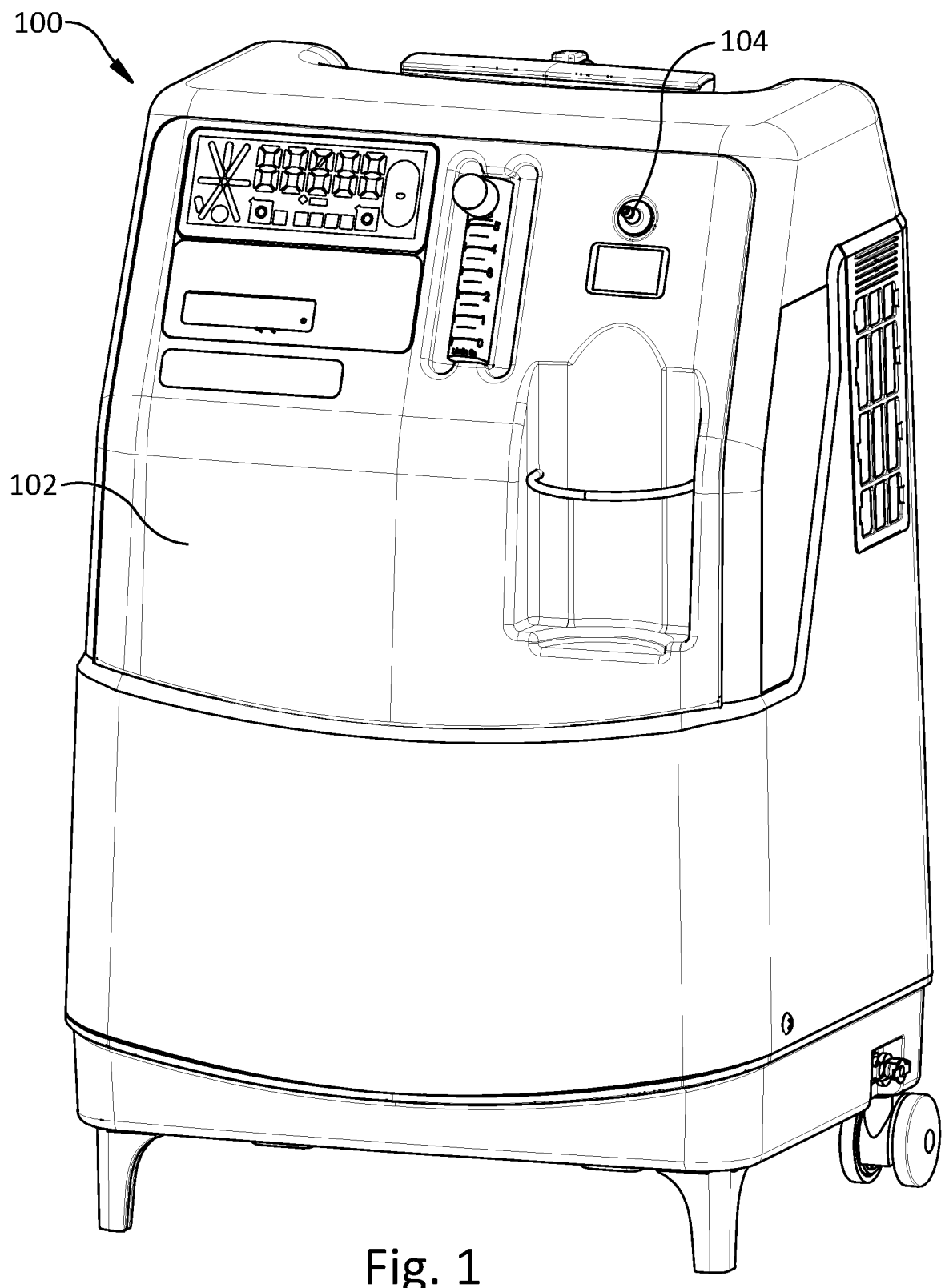
FIG. 1 shows one embodiment of a gas concentrating system and method.

As described herein, when one or more components are described or shown as being connected, joined, affixed, coupled, attached, or otherwise interconnected, such interconnection may be direct as between the components or may be indirect such as through the use of one or more intermediary components. Also, as described herein, reference to a member, component, or portion shall not be limited to a single structural member, component, element, or portion but can include an assembly of components, members, elements, or portions.

Embodiments of the present invention provide, for example, the ability to monitor sensors associated with operation of exemplary gas concentration systems and utilize information obtained from sensors throughout the system to perform certain data analysis tasks. Through analysis, the system may, for example, calculate a time to failure for one or more system components, generate alarms to warn a user of pending component failure, modify system settings to improve functionality in differing environmental conditions, modify system operation to conserve energy, and/or determine optimal settings configurations based on sensor feedback. Each of these examples will be described in further detail herein.

By way of example, oxygen concentrators utilize the pressure swing adsorption PSA technology to produce oxygen from air. The process is based on cycle steps that allow the pressure to swing from high to low and vice versa. The pressure differential is the driving factor for the generation of oxygen and the regeneration of the adsorbent. Some units operate based on a fixed shift time where all the cycles take the same durations. In the beginning of the unit life, the sieve is fresh, and the pressure drop in the bed is at its minimum. Other units operate under breakthrough conditions where the end of the adsorption time is determined by the impurity amount detected in the product tank. In those units the shift time decreases slowly over the life of the unit. The adsorbent performance depends on its selectivity, nitrogen capacity and diffusivity. The molecular sieve regeneration is essential to the concentrator life and oxygen amount produced. The absorbers get saturated over time by contaminants such as water vapor and carbon dioxide. This saturation is a degradation in the material capacity as the contaminants tend to occupy sites in the zeolite structure reducing the capacity to trap the Nitrogen. The main consequence of contamination is impurities (Nitrogen gas) breakthrough. The degradation in sieve material performance directly affects the amount of pure oxygen produced and therefore the oxygen purity delivered to the patient. Sieve bed health degradation can cause a decrease in oxygen purity and a gradual increase in the rate of pressurizing the tank. The product tank pressure, oxygen purity and time feedback can help monitor issues related to sieve beds.

As the adsorption capacity in the sieve beds decreases (due to wear from moisture, contaminants or abrasion), the amount of normal $N_2$ that is usually adsorbed and trapped in each cycle in the sieve bed will decrease (less bed capacity), causing the excess nitrogen not adsorbed to make a breakthrough from the oxygen side of the sieve beds. This breakthrough increases the total amount of impure gas in the product tank (reservoir or an accumulator) and therefore increases the pressure in the product tank and decrease the $O_2$ fraction from total volume. The amount leaving the product tank is usually controlled and fixed by the conserver valve timing for minute volume in a portable oxygen concentrator or the flowmeter in a stationary oxygen concentrator. In pressure shifting machines, the pressure of each shift is controlled and therefore the changing variable is the rate of reaching that target pressure. As the sieve bed wears the shift time will decrease due to reaching the target pressure faster with higher volume of impurities in the tank. In order to detect that the $O_2$ degradation is due to the sieve bed wear and not other failures, the pressure in the product tank (in a time shifting device) can be monitored. A gradual increase in pressure in combination with a decrease in $O_2$ is only present in the case of sieve bed wear. The rate of pressure, $O_2$ change, and time can be used as a feedback for sieve bed health monitoring. Other unique component failures (e.g., pumps, valves, etc.) can also be determine through analysis of pressure and/or oxygen sensor signals to generate alarms, warnings, and time to failure estimates.

By way of example, one or more component specific alarms associated with component failure, a failing component, or a time to failure can be determined by utilizing one or more sensor signals. For example, oxygen and/or pressure sensors can be used to determine sieve bed and/or compressor failure and/or predict time to failure. Pressure signals can be used to determine main valve failure and/or predict time to failure. Pressure waveforms into or out of the oxygen product tank, in combination with low oxygen purity levels, can be used to determine check valve failure and/or predict time to failure. Linear regression analysis applied to pressure versus time slope data can determine a predicted time to system (or sieve bed) failure when the operating pressure will exceed acceptable value(s). Similarly, a linear regression analysis applied to oxygen concentration versus time slope data can determine a predicted time to system (or sieve bed) failure when the oxygen concentration will fall below acceptable value(s). Electrical output signals (including the absence thereof and/or out of range signals) of various sensors including oxygen and pressure sensors can be used to determine sensor failure and/or predict time to failure.

In one embodiment, the time to failure is determined by using a linear regression analysis to predict the time at which the system and/or component will no longer provide an adequate output or operating parameter. For example, linear regression analysis of system pressure and/or oxygen data (e.g., high, low, decaying over time, rising over time, combinations of the foregoing, etc.) can be used to identify and predict the time to failure of one or more components. This is because system components such as valves, motors, pumps, sieve beds, and sensors, when starting to fail or fail, each cause a unique effect or combination of effects on overall system behavior and function allowing for the identification of the failing component(s) and a predicted time to failure through linear regression analysis. These unique effects or combination of effects are discussed in more detail below.

Illustrated in FIG. 1 is one embodiment of an oxygen system 100, which includes component failure analysis and/or alarms. The system may be stationary such as, for example, for use in a hospital or a patient's home. The system can also be ambulatory or mobile such as, for example, for use by a patient when they are away from home. The system can be configured in a manner to allow the patient to carry the system such as, for example, through an over the shoulder strap or through an arrangement whereby the system includes a handle and wheels. Other mobility configurations are also included.

Oxygen system 100 includes a housing 102, which can be in one or more sections. Housing 102 includes a plurality of openings for the intake and discharge of various gases such as, for example, the intake of room air and the discharge of nitrogen and other gases. Oxygen system 100 generally intakes room air, which is mostly comprised of oxygen and nitrogen, and separates the nitrogen from the oxygen. The oxygen is stored in one or more internal or external storage or product tanks and the nitrogen is discharged back into the room air. For example, the oxygen gas may be discharged through port 104 to a patient through tubing and nasal cannula. Alternatively, the oxygen gas may be discharged through a supplemental port to an oxygen cylinder filling device, such as HOMEFILL® that is manufactured by Invacare Corp. of Elyria, Ohio, USA.

Figure 2:
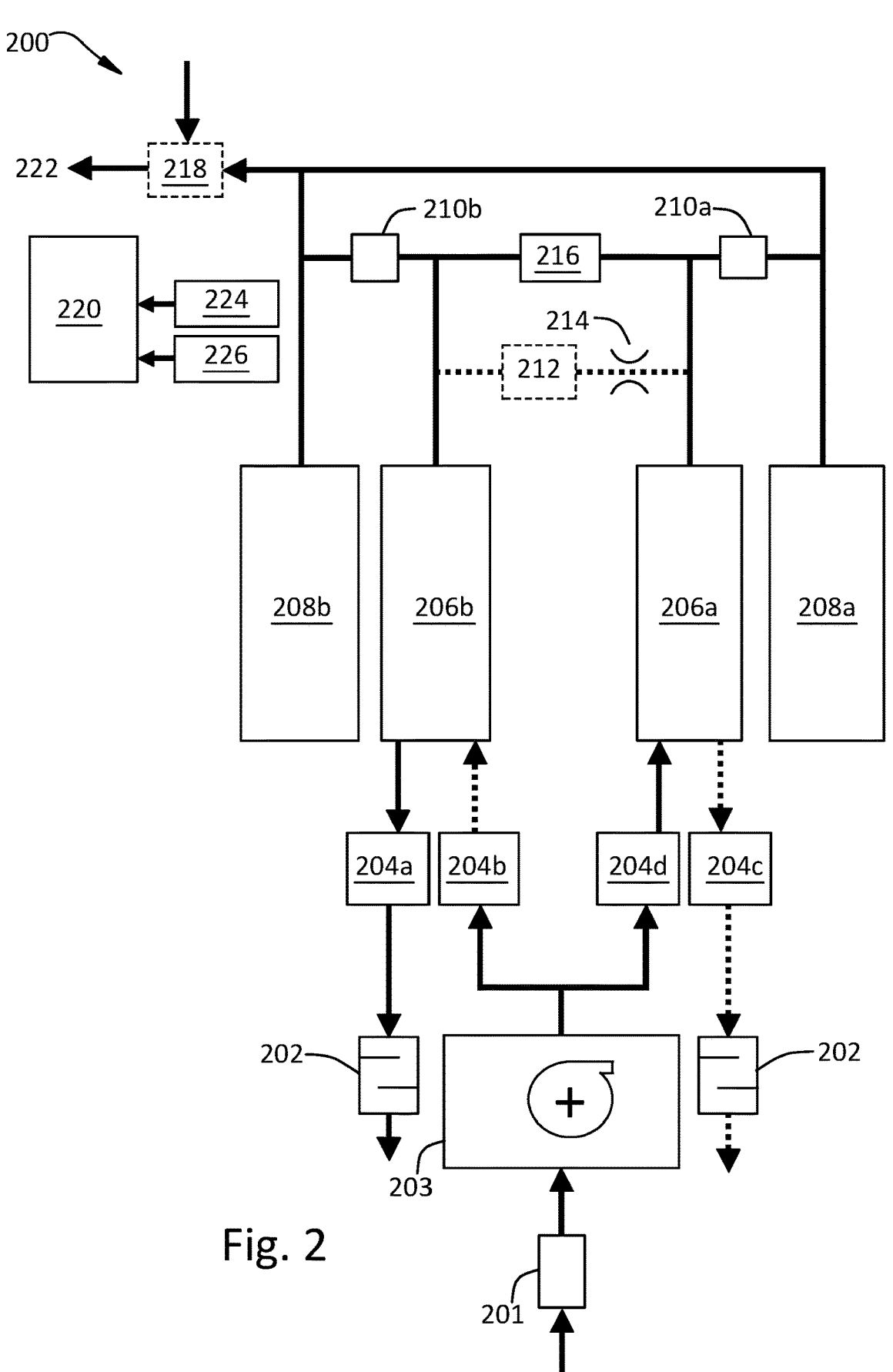
FIG. 2 is one embodiment of a pneumatic block diagram of a gas concentrating system and method.

FIG. 2 illustrates one embodiment of an exemplary pneumatic block diagram for a gas concentrating system 200 using pressure swing adsorption (PSA). The system can include multiple gas separation sieve beds 206a and 206b, multiple valves 204a, 204b, 204c, and 204d, one or more product tanks 208a, 208b and a conserver valve/device 218. In this embodiment, product tanks 208a, 208b are shown connected so they act as one product tank but may also be arranged to act as two product tanks. The system also includes compressor/pump 203 and one or more filters 201 and mufflers 202.

Sieve beds 206a and 206b are filled with a physical separation medium or material. The separation material selectively adsorbs one or more adsorbable components and passes one or more nonadsorbable components of a gaseous mixture. Generally, the physical separation material is a molecular sieve with pores of uniform size and essentially the same molecular dimensions. These pores selectively adsorb molecules in accordance with molecular shape, polarity, degree of saturation, and the like. In one embodiment, the physical separation medium is an aluminasilicate composition with 4 to 5.ANG. (Angstrom) pores. More specifically, the molecular sieve is a sodium or calcium form of aluminasilicate, such as type 5A zeolite. Alternately, the aluminasilicate may have a higher silicon-to-aluminum ratio, larger pores, and an affinity for polar molecules, e.g., type 13x zeolite. The zeolite adsorbs nitrogen, carbon monoxide, carbon dioxide, water vapor, and other significant components of air. Other types of separation media may also be used. Also, more than two sieve beds can be used. In other embodiments, the sieve beds 206a and 206b can be structurally integrated with one or more product tanks 208a and 208b, such as described in U.S. Pat. No. 8,668,767, which is hereby fully incorporated by reference for this and other features.

In operation, as shown by the solid lines in FIG. 2, during an exemplary fill cycle of separation bed 206a, pump/compressor 203 draws room air through filter 201 and to valve 204d and separation bed 206a, which produces oxygen at its output and into product tanks 208a, 208b through valve 210a. Pump/compressor 203 supplies air up to about 32 pounds per square inch during the fill phase to a sieve bed. Other working pressure ranges including about 15-34 pounds per square inch. Valves 210a and 210b may be check valves or any other similarly functioning valve that allows only one-way flow.

While separation bed 206a is undergoing the fill cycle, separation bed 206b may be undergoing a purge cycle to expel any nitrogen gas from a previously fill cycle. During the purge cycle, previously pressurized separation bed 206b expels nitrogen gas through valve 204a and out to atmosphere through muffler 202. Separation bed 206b is pressurized from its previous fill cycle. During the purge cycle, an amount of oxygen from separation bed 206a or product tanks 208a, 208b can be fed into separation bed 206b to preload or pre-charge separation bed 206b with oxygen, as controlled by optional bleed valve 212 and fixed orifice 214, shown in FIG. 2 with dashed lines.

As shown by the dotted lines in FIG. 2, once separation bed 206a has been filled and/or separation bed 206b has been purged, control system 220 switches valves 204a, 204b, 204c, and 204d so that separation bed 206b enters the fill cycle while separation bed 206a enters the purge cycle. In this state, pump 203 directs room air into separation bed 206b, which produces oxygen at its output and into product tanks 208a, 208b through valve 210b. Separation bed 206a is undergoes a purge cycle whereby it discharges nitrogen and other gases our valve 204c and muffler 202 to the atmosphere or room. During the purge cycle, an amount of oxygen from separation bed 206b or product tanks 208a, 208b can be fed into separation bed 206a to preload or pre-charge the separation bed 206a with oxygen, now flowing in the opposite direction as compared to the previous cycle. The illustrated system also includes an exemplary pressure equalization valve 216, which equalizes the pressure in the two separation beds prior to a purge/fill cycle change.

The pressure equalization valve 216 can allow for a more efficient generation of oxygen by equalizing the pressure between the outputs of a separation bed (e.g., 206a) nearing the end of its fill cycle and a separation bed (e.g., 206b) nearing the end of its purge cycle. For example, pressure equalization valve 216 may be activated to equalize the pressure between the outputs of separation bed 206a and separation bed 206b near the end of each purge/fill cycle. U.S. Pat. Nos. 4,449,990 and 5,906,672, which are fully incorporated herein by reference, further describe the operation of pressure equalization valves. In this manner, each separation bed 206a, 206b cyclically undergoes alternating fill and purge cycles as controlled by control system 220 to thereby generate oxygen.

As shown in FIG. 2, optional conserver valve/device 218 may be used to control the delivery of product gas to a user 222. Conserver valve 218 may switch between providing concentrated product gas from the product tanks 208a, 208b or venting to the room air. For example, the conserver valve 218 may be used to selectively provide various continuous or pulsed flows of concentrated oxygen product gas in an amount and at a time determined by the control system 220. This time is typically based on sensing an inhalation by the user and is typically determined by sensing a drop in pressure or (increase in flow) proximate the user's nose or mouth.

In this embodiment, control system 220 may utilize various control processes to optimize the production and delivery of concentrated product gas by controlling the activation, levels, and relative timing of pressure source 203 and valves 204a, 204b, 204c, 204d, 216, and 212, for example. This is accomplished by use of one or more pressure sensor(s) 224 and/or oxygen concentration sensor(s) 226. In one embodiment, pressure and oxygen sensors 224 and 226 monitor the pressure and oxygen concentration entering product tank(s) 208A and 208(b). In other embodiments, use of timed cycles can be employed wherein the cycle times are set at the factory. In further embodiments, the cycle times can be determined from flow settings and/or sensed patient flow demands. In yet further embodiments, the cycle times can be determined during a startup diagnostic procedure when the oxygen concentrator is turned or powered on.

While FIG. 2 illustrates a pressure swing adsorption (PSA) cycle, other gas concentrating cycles may also be used including vacuum swing adsorption (VSA), vacuum-pressure swing adsorption (VPSA) or other similar modes. The particular gas concentrating mode is not critical to the embodiments of the invention described herein so long as they are capable of producing a concentrated gas such as oxygen to the user. Examples of the above modes of operation are disclosed in, for example, U.S. Pat. Nos. 9,266,053 and 9,120,050 which have been fully incorporated by reference.

Due to the mechanical nature of many of the system components, component wear and failure can occur. However, determining time to failure and diagnosing which components have failed is time consuming and inefficient. Embodiments of the present inventions analyze factors and component failures that can cause oxygen purity and/or operating pressures to change. In one embodiment, the systems and methods analyze pressure and/or oxygen sensor data to determine sieve bed wear and predict time to failure. In one example, a gradual increase in separation or sieve bed operating pressure in combination with a decrease in oxygen purity over time is a distinct failure mode associated with sieve bed wear. In other examples, operating pressure can be used alone to determine a predicted time to system or sieve bed failure by using linear regression analysis on the pressure versus time slope data to determine when it will increase beyond a threshold value (e.g., 34 PSI or some other value). Similarly, oxygen concentration/purity can be used alone to determine a predicted time to system or sieve bed failure by using linear regression analysis on the oxygen purity versus time slope data to determine when it will decrease below a threshold value (e.g., 85% or some other value). In yet other example, the pressure and oxygen linear regressions can be both be separately determined and the predicted time to failure can be set to be the sooner of the two determinations (e.g., time to reach low oxygen threshold or time to reach high pressure threshold), which would then trigger a warning that the sieve bed(s) need to be replaced or replaced soon.

Other distinct component failures can also be identified. These include the airside (main) valves (e.g., 204a, 204b, 204c, and/or 204d) being stuck closed or open. These failures cause oxygen purity to drop (e.g., below 85%, below 73%, etc.) along with an immediate pressure change (i.e., not gradual) on the input (or output) of the sieve bed(s). An airside (main) valve leak can be distinctly identified by low oxygen purity (e.g., below 85%, below 73%, etc.) coming out of the sieve bed and a lower (out of range) sieve bed operating pressure. A check valve leak can be distinctly identified by low oxygen purity (e.g., below 85%, below 73%, etc.) and a product tank pressure "v" shape decrease. A tubing leak can be identified by low oxygen purity (e.g., below 85%, below 73%, etc.) and low (e.g., out of range) system pressure(s). Compressor wear can be distinctly identified by low oxygen purity (e.g., below 85%, below 73%, etc.) and low input and output (e.g., out of range) sieve bed pressures. An obstruction/restriction on flow causes immediate high system pressures (e.g., out of range) and oxygen purity that stays the same or gets higher. A flow output setting change can be identified by pressure and oxygen purity: an increase in flow setting causes pressure (e.g., system or product tank) to go down and oxygen purity to go down slightly, and a decrease in flow setting causes pressure (e.g., system or product tank) to go up and oxygen purity to go up. These and other sensed parameters can be used to diagnose component failure and/or time to failure.

Figure 3:
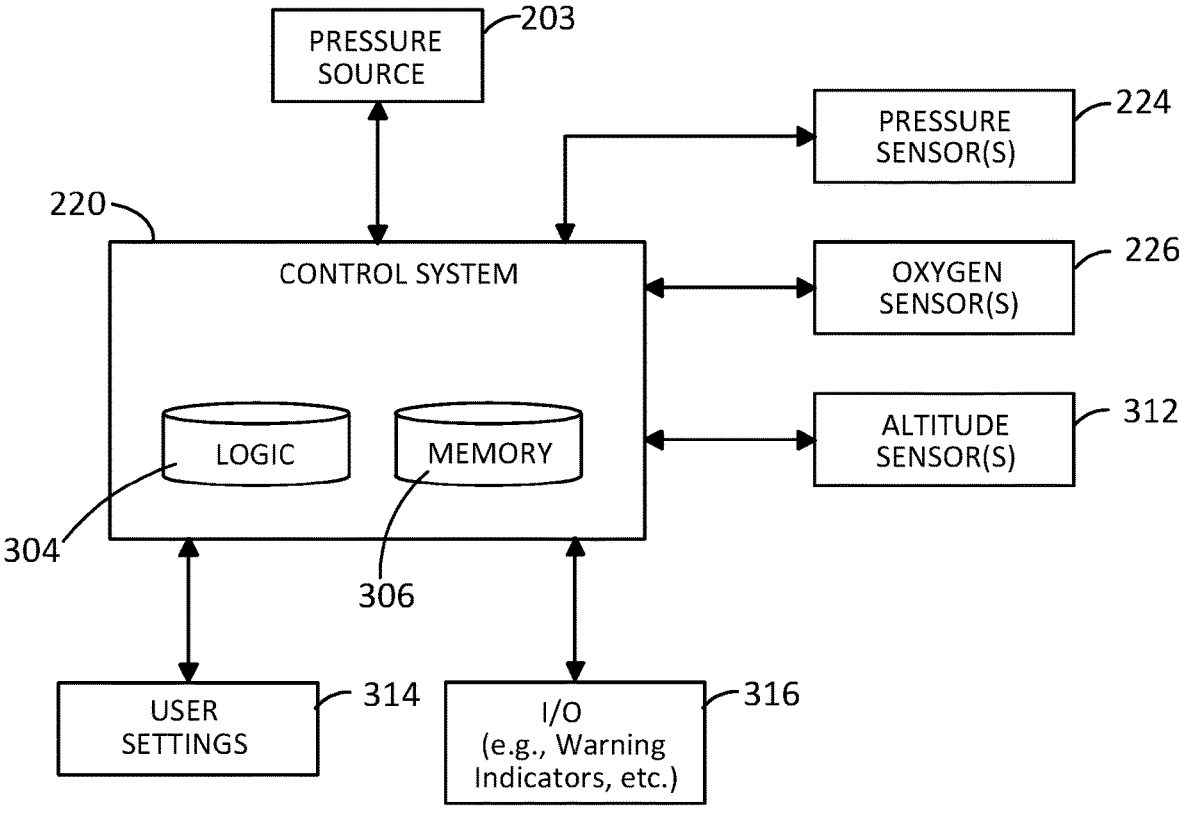
FIG. 3 is one embodiment of a controller of an exemplary gas concentrating system and method.

FIG. 3 illustrates a detailed view of one embodiment of a control system 220 having component failure logic. While described herein with specific reference to exemplary gas concentrating systems, it is appreciated that control system 220 may be readily adapted for use with additional systems. In certain embodiments, control system 220 may be operatively connected to and/or in data communication with one or more sensors, for example, pressure sensor(s) 224, oxygen sensor(s) 226, and/or altitude sensor 312. Other sensors may also be used including, for example, flow and/or temperature sensors. Pressure sensor(s) 224 may be associated with various components of an exemplary gas concentrating system (e.g., gas concentrating system 200) and are configured to measure pressure in real-time or near real-time. In certain embodiments, pressure sensor(s) 224 may comprise an individual sensor configured to monitor and collect pressure data from multiple components. Similarly, oxygen sensor(s) 224 may be associated with various components of an exemplary gas concentrating system (e.g., gas concentrating system 200) and are configured to measure oxygen values in real-time or near real-time. In certain embodiments, oxygen sensor(s) 226 may comprise an individual sensor configured to monitor and collect pressure data from multiple components. Altitude sensor 312 may comprise an altimeter, barometric sensor, or the like configured to measure the physical altitude of the gas concentrating system. It is appreciated that additional sensors may be operatively connected to and/or in data communication with control system 220. In some embodiments, control system 220 is configured to implement control schemes to optimize the production and delivery of concentrated product gas by controlling the activation, levels, and relative timing of pressure source 203 and, in some embodiments, valves 204a, 204b, 204c, 204d, 216, and 212 (see FIG. 2). Control system 220 may be additionally be operatively connected to and/or in data communication with a user settings module 314. User settings module 314 is configured to communicate various user settings to control system 220. In some embodiments, user settings module 314 may receive user input from a user input device, such as, for example, a computer, tablet, smartphone, or the like. In other embodiments, user settings module 314 may receive user input via a control panel or the like associated with an exemplary gas concentrating system (e.g., gas concentrating system 200). In some embodiments, initial settings may be set by the manufacturer as "default" settings which may be stored in memory, e.g., memory 306.

Control system 220 also communicates with various input/output devices 316. Input and output devices include pushbuttons on the housing of the oxygen concentrator, wireless devices (e.g., tablets, smartphones, laptops, remote servers, RFID tags, readers, writers, etc.). devices connected through one or more communication ports (e.g., serial bus ports (e.g., USB, etc.), memory card slots (e.g., SD, etc.), etc.), light emitting devices (e.g., lamps, LED's, etc.), speakers for audio output, microphones for audio input, cameras, etc.

In one embodiment, pressure sensors are associated with the inputs and/or outputs of the sieve bed(s) 206a, 206b. Pressure sensors can further be associated with the input and/or output of one or more product tanks 208a, 208b. Similarly, oxygen sensors can be associated with the input and/or output of one or more product tanks 28a, 208b. Oxygen sensors can also be associated with the output(s) of one or more sieve beds 206a, 206b. Other components can also have the pressure and/or oxygen sensors associated them as well.

Control system 220 comprises at least logic 304 and memory 306 for component failure analysis. Logic 304 may further comprise one or more processors or the like operable to perform calculations and other data analysis, such as, for example, regression analysis. It is appreciated additional types of data analysis may be performed by control system 220 using via logic 304, for example, linear regression (e.g., $Y=bx+a$), exponential trendline (e.g., $Y=ae^{bx}$), logarithmic trendline (e.g., $Y=a*ln(x)+b$), polynomial trendline (e.g., $Y=b6x^6+ \ldots +b1x+a$), power trendline, etc. In certain embodiments, multiple data analyses may be used in combination, for example, a linear regression may be performed for small sections of a polynomial model. In some embodiments, control system 220 may utilize logic 304 to perform analysis of data received from sensors associated with the gas concentrating system, for example, pressure sensor(s) 224, oxygen sensor(s) 226, and/or altitude sensor(s) 312. Through analysis of data received from such sensors, control system 220 may identify and diagnosis failing components before total failure allowing for better diagnostic maintenance and repair, more efficient service and repair, and cost savings related to wrongly replace components (e.g., targeted repair).

Figure 4:
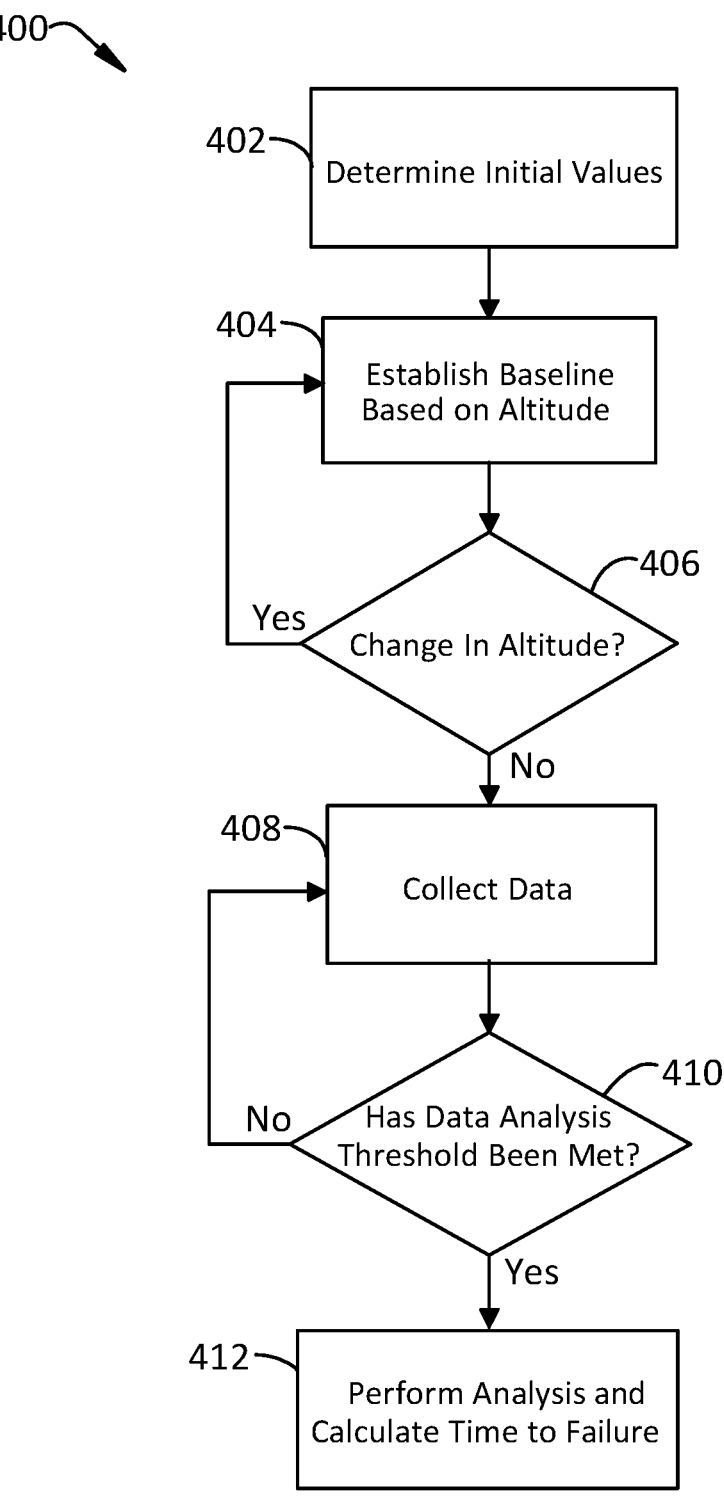
FIG. 4 is one example of an exemplary method for calculating a time to failure for at least one component of a gas concentrating system.
Figure 5:
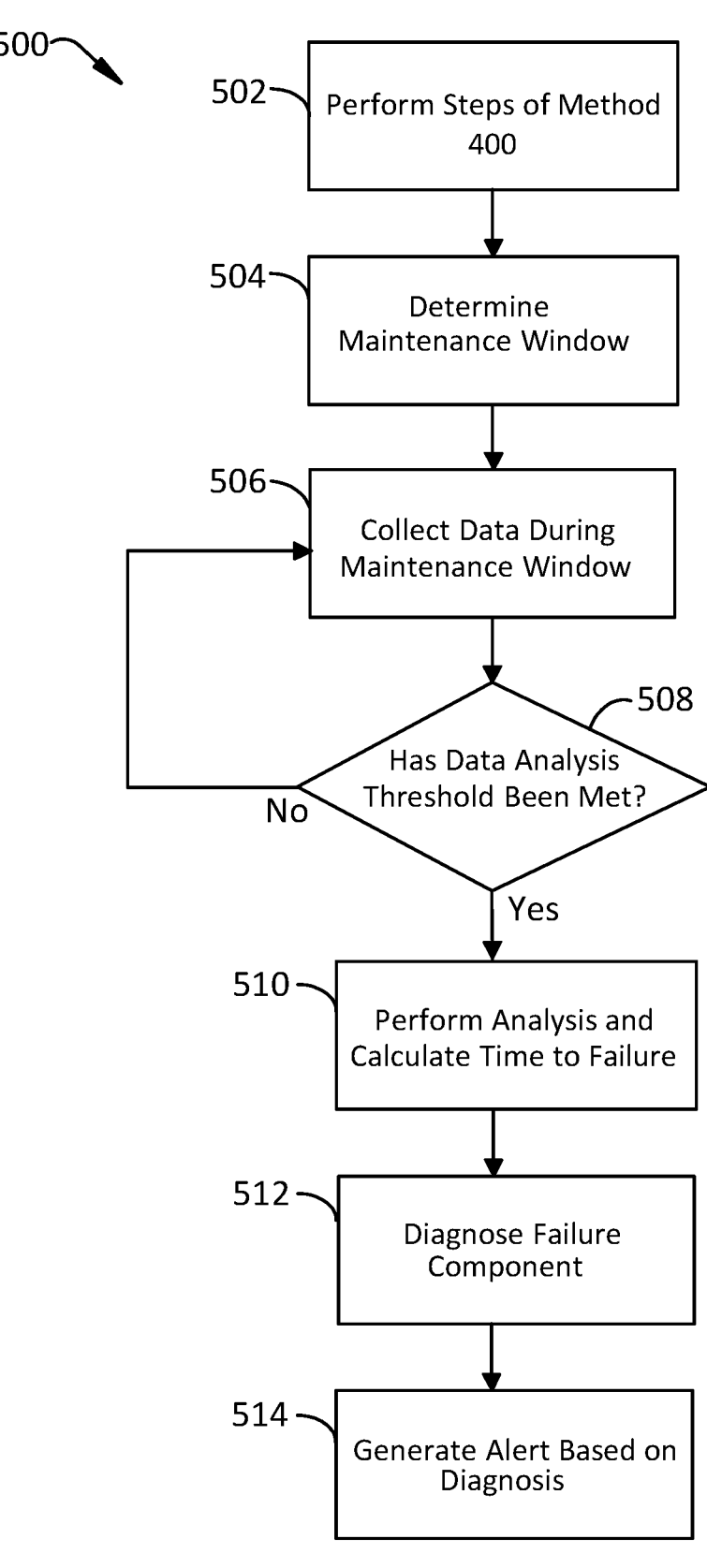
FIG. 5 is one example of an exemplary method for diagnosing failure of one or more components in a gas concentrating system.

FIGS. 4-6 illustrate various examples of logic for such data analysis methods performable by controller 220. It will be appreciated that the illustrated methods and associated steps may be performed in a different order, with illustrated steps omitted, with additional steps added, or with a combination of reordered, combined, omitted, or additional steps.

In FIG. 4, one embodiment of a method 400 for calculating a time to failure for at least one component of a gas concentrating system is shown. The method 400 begins at 402 wherein initial values are determined. Initial values may comprise an oxygen level as measured by one or more oxygen sensors (e.g., oxygen sensor(s) 226), a pressure level as measured by one or more pressure sensors (e.g., pressure sensor(s) 224), and/or an altitude as measure by an altitude sensor (e.g., altitude sensor 312). It is appreciated that initial values may be determined at a specific time (e.g., 30 seconds after the gas concentrating system is ready for operation) or, in the alternative, initial values may comprise an average of several measurements taken after the gas concentrating system is ready for operation. In some embodiments, block 402 additionally comprises a startup check after warmup, for example, determining a steady state of oxygen after it is done increasing and not after it reaches a predetermined ready threshold (e.g., 85%). It is not unusual for the system to require several cycles as a warm-up or start-up to steady-state operation.

At block 404, a baseline of values is established based on the altitude of the gas concentrating system. This baseline of values may comprise oxygen and pressure levels at one or more locations throughout the system (e.g., sieve beds, product tank, valves, compressor, etc.) The altitude may be determined based on the measured altitude, or in some embodiments, may be determined based on a user setting (e.g., an altitude zone such as "high altitude" or low or "sea level"). In one example: an exemplary gas concentrating system can have 6 altitude zones: sea level, 4000 ft, 6000 ft, 8000 ft, 10000 ft, 13,000 ft, each with a +/−500 ft range. Each range can have multiple combinations with various flow settings: 1, 2, 3, 4, or 5 LPM. With these settings, there can be up to 30 states. For each state, certain data points are collected to estimate a decay equation. Altitude zones can be used as a feedback to increase pressure as needed (for example at lower flow settings when fill/purge shift times become short, a high altitude zone feedback can be used to increase the time and therefore the pressure in the tank to avoid a valve getting stuck below minimum operating limits. Once the baseline of values is determined at a given altitude, the baseline is stored (e.g., in memory 306) and method 400 continues to block 406. At block 406, it is determined if there has been a change in altitude. If there has been a change in altitude, method 400 returns to block 404 to establish a new baseline based on the new altitude. It is appreciated that a change in altitude may be measured or may comprise a change in a user setting associated with altitude (e.g., a change in altitude zone setting). In some embodiments, altitude is measured during a predetermined increment (e.g., every 24 hours). In certain embodiments, the change in altitude may be measured according to various thresholds of altitude, for example, according to predetermined altitude zones. In such embodiments, a change in altitude will only be determined if the measured altitude changes the range of altitudes that define a specific altitude zone. In some embodiments, altitude changes may account for hysteresis and tolerance for a given zone (e.g., +/−500 ft).

If no change in altitude is determined at block 406, the method continues to block 408. At block 408, data, for example, additional oxygen and pressure values, are collected and stored (e.g., in memory 306). It is appreciated that oxygen and pressure values may be collected for components of the gas concentrating system individually or in combination. For instance, data may be collected for an individual value and/or for a collection of valves over time and/or at certain time intervals. In some embodiments, data values are captured and stored according to a predetermined sample time (e.g., every 1 hour). In some embodiments, the sample time may be modified by controller 220 based on operating conditions and/or measured value. For example, if the measured oxygen values dip below a threshold, the sample time may be increased so as to more closely monitor changes in measured values. In one exemplary embodiment, if the measured oxygen values dip below 89%, the sample time may be increased to collect samples every 10 minutes instead of every 1 hour. It is appreciated that additional sample intervals and thresholds are contemplated and the above is offered by way of example only.

At block 410, it is determined if a data analysis threshold has been met. The threshold for data analysis may vary according to operating conditions, factory settings, and/or user settings. It is appreciated that additional sample size results in more precise analysis. If a threshold has not been met, the method returns to step 408 to collect additional data points. Once a sufficient number of data points have been collected, the method continues to block 412.

At block 412, analysis of the data points is performed by control system 220 (e.g., via logic 304) and a time to failure is calculated. Various methods of data analysis are contemplated herein. In some embodiments, the analysis comprises performing a linear regression function (e.g., calculating the slopes and intercepts of oxygen and pressure as a function of time). An exemplary linear regression analysis for oxygen values ($O_2$) is expressed in Formula 1.

$$Sum Y = sum(O_2)$$

$$Sum X = sum (Hours)$$

$$XY = O_2 * Hours$$

$$XX = Hours^2$$

$$YY = O_2^2$$

$$Sum XX = sum(XX)$$

$$Sum YY = sum(YY)$$

$$Sum XY = sum(XY)$$

$$a = ((Sum Y * Sum XX) - (Sum X * Sum XY)) / ((20 * Sum XX) - (Sum X)^2)$$

$$b = ((20 * Sum XY) - (Sum X) * (Sum Y) / (20 * (Sum XX) - (Sum X)^2)$$

Formula 1: Oxygen Linear Regression Calculations

An exemplary linear regression analysis for pressure values (Pressure) is expressed in Formula 2.

$$Sum Y = sum(Pressure)$$

$$Sum X = sum (Hours)$$

$$XY = Pressure * Hours$$

$$XX = Pressure^2$$

$$XY = O_2^2$$

$$Sum XX = sum(XX)$$

$$Sum YY = sum(YY)$$

$$Sum XY = sum(XY)$$

$$a = ((Sum Y * Sum XX) - (Sum X * Sum XY) / ((20 * Sum XX) - (Sum X)^2)$$

$$b = ((20 * Sum XY) - (Sum X) * (Sum Y)) / (20 * (Sum XX) - (Sum X)^2)$$

Formula 2: Pressure Linear Regression Calculations

From the above linear regression calculations, it is possible to determine a time to failure value. A time to failure may be expressed as the number of hours until one or more components of the gas concentrating system fail. In certain embodiments, linear regression calculations can be performed for components of the gas concentrating system individually or in combination. In some embodiments, linear regression calculations may be calculated multiple times as updated data is collected, for example, after a number of data points sufficient for data analysis are collected (e.g., every 20 new data points). Each linear regression calculation may be stored in memory (e.g., memory 306). Stored regression calculations may be compared or similarly analyzed to draw conclusions about and/or diagnose problems relating to one or more components of the gas concentrating system. It is appreciated that certain components of the gas concentrating system may exhibit certain characteristics (e.g., unusual oxygen or pressure values) that indicate degradation or failure of the component which can lead to suboptimal operation of the gas concentrating system. In certain embodiments, time to failure is calculated for a single component. In other embodiments, time to failure is calculated for a plurality of components. In certain other embodiments, time to failure is calculated for every component for which data is collected. Through further analysis of data, it is possible to diagnose failure of specific components of the gas concentrating system.

FIG. 5 illustrates an exemplary method 500 for diagnosing failure of one or more components in a gas concentrating system. The method 500 begins at block 502 wherein method 400 is performed. As described herein, method 400 concludes with performing analysis and calculating a time to failure for at least one component of the gas concentrating system. At block 504, a maintenance window is determined. Determining a maintenance window comprises calculating a window of time before the calculated time to failure. This maintenance window of time could potentially allow for mitigation of a problem that would eventually lead to failure of a component if left unchecked (e.g., 30 day or 720 hour window of time before predicted time to failure). In certain embodiments, the maintenance window is calculated in "moving hours" meaning the time window can change depending on updated data or time to failure.

At block 506, data is collected during the maintenance window. The data collected in block 506 may comprise oxygen and/or pressure data. At block 508, it is determined if the data analysis threshold has been met. In some embodiments, the data analysis threshold may require only a single measurement taken at the beginning of the maintenance window. Once a sufficient amount of data has been collected, the method proceeds to block 510. At block 510, data analysis is performed and an updated time to failure is calculated. In certain embodiments, block 510 comprises calculating a linear regression for oxygen and/or pressure data for one or more components of the gas concentrating system (e.g., see Formulas 1 and 2 above). At block 512, the method diagnoses a failure component.

Based on analysis of collected data and linear regression calculations, it is possible to identify a failure component and diagnose the problem with said component. For example, if the linear regression of pressure data calculated at the beginning of the maintenance window results in a negative slope, the decay in oxygen readings can be linked to compressor or filter failure. Alternatively, if the linear regression of pressure data at the beginning of the maintenance window yields a positive slope, the decay in oxygen readings is indicative of a sieve bed failure. As another example, if the linear regression of pressure data calculated at the end of the maintenance window yields a negative slope, the decay in oxygen readings can be linked to compressor or filter failure. In the alternative, if the linear regression of pressure data calculated at the end of the maintenance window yields a positive slope, the decay in oxygen readings can be linked to sieve bed failure.

Many additional diagnoses are contemplated herein. For example, a measured drop in oxygen purity and immediate pressure change can indicate an airside valve failure (e.g. stuck open/closed). Similarly, if low oxygen purity is accompanied by lower pressure on one side of the sieve beds, it can indicate that one of the airside valves is leaking. When low oxygen purity is observed along with product tank pressure experiencing a "V" shaped decrease, it is indicative of a check valve leak. When low oxygen purity is observed along with low pressure it can indicate a tube leak. When low oxygen and low pressure is observed on both sides of the sieve beds, it is indicative of compressor failure. When an immediate pressure increase is observed while oxygen purity stays the same or increases, it is indicative of an obstruction on flow (e.g., a restriction). When the pressure increases immediately along with oxygen purity, it is indicative of a flow settings change. When the observed pressure experiences a gradual increase in combination with a decrease in oxygen over time, it is indicative of sieve bed failure. It is appreciated that the above examples are offered for illustrative purposes only and are not limiting to the scope of the present embodiments.

In some embodiments, component failure may be diagnosed using data observed from electrical signals. For example, a drop in an electrical voltage signal on the driver of each component can be used to evaluate if a coil in a valve is faulty. Similarly, a drop in electrical voltage may indicated that a component has loose or disconnected wires in the printed circuit board (PCB).

It is appreciated that block 512 may comprise additional data analysis (e.g., time since last maintenance, component manufacture date, etc.) to further assist in diagnosis component failure.

After a diagnosis is made, the method continues to block 514. At step 514 an alert or warning is generated based on the diagnosis. In some embodiments, the alert comprises information relating to the diagnosis, such as, for example, the identified component, latest calculated time to failure, the specific failure (which may comprise displaying an error code or message), the severity of the failure, etc. The alert may trigger certain activity associated with the gas concentrating system. For example, an alert may cause a chime, buzz, or similar sound to alert a user of the detected failure. In certain embodiments, the alert is displayed on a display associated with the gas concentrating system. In some embodiments a failure alert may trigger a notification to be sent to a user's smartphone. Similarly, a notification may also be sent to a provider that is responsible for service and maintenance of the gas concentrating system. In certain embodiments, alert information may be transmitted to a server via an internet connection or the like for storage and analysis by a provider or the manufacturer. Analysis of alert information can provide valuable information relating to the operation of the gas concentrating system in different environments.

Figure 6A:
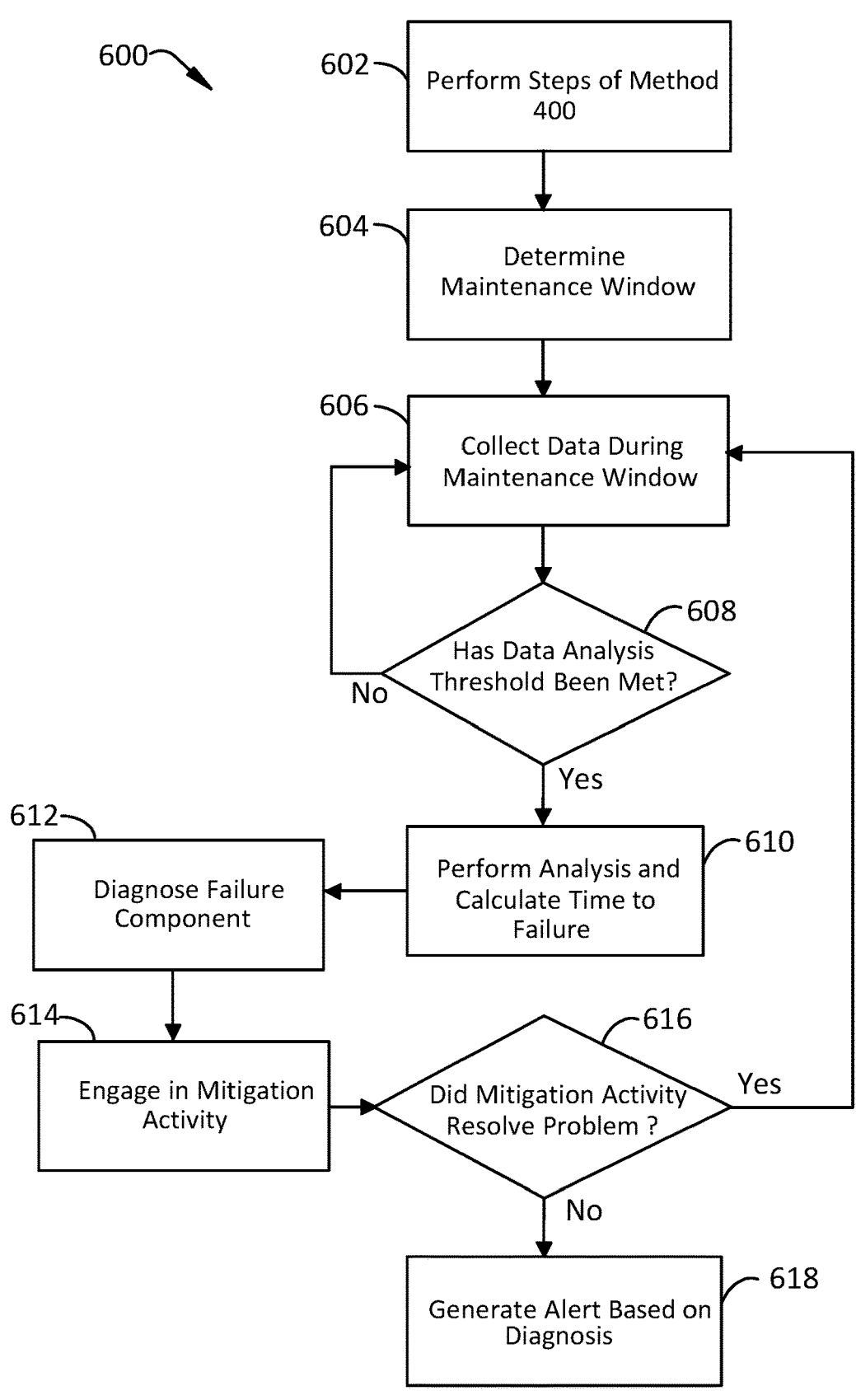
FIGS. 6A-6B illustrate various embodiments of methods and logic for diagnosing the failure, predicted failure and/or health of one or more components in a gas concentrating system.

FIG. 6A illustrates another exemplary method 600 for diagnosing failure of one or more components in a gas concentrating system. The method 600 begins at block 602 wherein method 400 is performed. As described herein, method 400 concludes with performing analysis and calculating a time to failure for at least one component of the gas concentrating system. At block 604, a maintenance window is determined. Determining a maintenance window comprises calculating a window of time before the calculated time to failure that could potentially allow for mitigation of a problem that would eventually lead to failure of a component if left unchecked (e.g., 30 days or 720 hours to failure). In certain embodiments, the maintenance window is calculated in "moving hours" meaning the time window can change depending on updated data.

Figure 7:
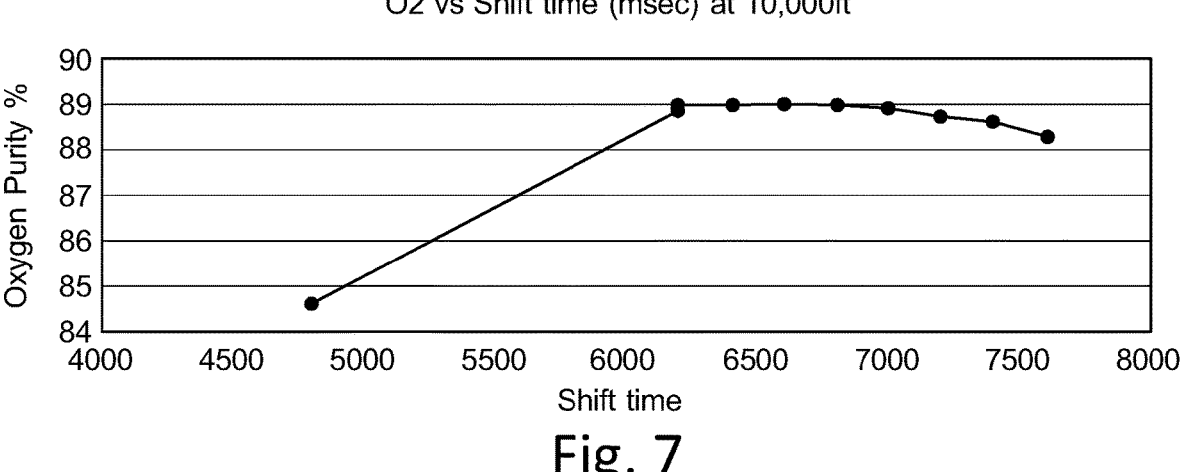
FIG. 7 is a chart illustrating exemplary values of oxygen purity at an extreme environmental condition (e.g., 10,000 ft about sea level) when modifying shift time of the oxygen producing process.

At block 606, data is collected during the maintenance window. The data collected in block 606 may comprise oxygen and/or pressure data. At block 608, it is determined if the data analysis threshold has been met. In some embodiments, the data analysis threshold may require only a single measurement taken at the beginning of the maintenance window. Once a sufficient amount of data has been collected, the method proceeds to block 610. At block 610 data analysis is performed and an updated time to failure is calculated. In certain embodiments, block 610 comprises calculating a linear regression for oxygen and/or pressure data for one or more components of the gas concentrating system. At block 612, the method diagnoses a failure component. Based on the diagnosis, the method may continue to block 614, where a mitigation activity is performed. A mitigation activity may comprise any activity engaged in to potentially resolve a problem with one or more components of the gas concentration system. For example, high altitude can contribute to lower oxygen purity as the overall working pressure decreases. If these conditions are present and a related failure is detected and/or diagnosed, the oxygen concentration system (via controller 220) can modify valve shift time thereby optimizing oxygen purity production given the environmental conditions. Adjusting the pressure equalization time and shift time can be done to increase the oxygen purity in extreme environmental conditions (e.g., high altitude), high pressure increase as a result of wear and/or failure of the sieve beds, low pressure as a result of wear and/or failure of the compressor, and/or low oxygen in general. For each of these situations, pressure can be maintained and used as a main feedback along with altitude by changing valve timing. For example, an increase in the shift time/pressure equalization time can increase system and/or component pressure whereas a decrease in the shift time/pressure equalization time can decrease system and/or component. FIG. 7 illustrates exemplary values of oxygen purity at an extreme environmental condition (e.g. 10,000 ft about sea level) when modifying shift time.

Figure 6B:
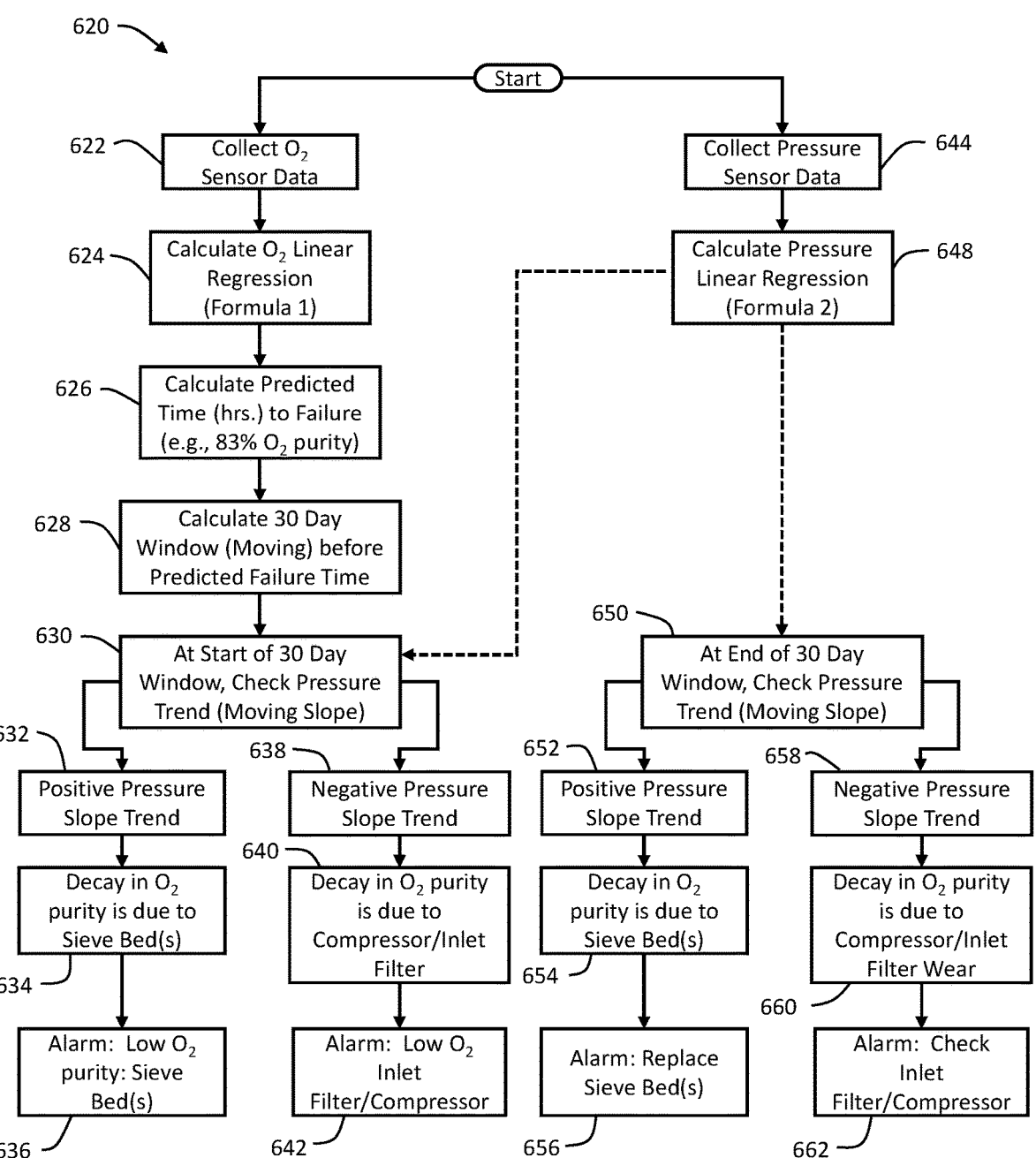

FIG. 6B illustrates one embodiment 620 of logic for analyzing the health of sieve beds and/or compressors. This embodiment uses regression analysis as previously described to determine a predicted time to failure and moving slope analysis to identify the component (e.g., sieve beds and/or compressors) which is failing or predicted to fail soon. The logic begins in blocks 622 and 644 where oxygen and pressure sensor data are collected during warm-up or normal system operation. In blocks 624 and 648, a linear regression analysis as previously described is performed on each set of data. In block 626, the logic calculates a predicted time to failure (in e.g., hrs.) by determining when the oxygen purity level will according to the regression analysis be at or below 83% purity (e.g., concentration). In block 638, the logic calculates a 30-day moving window that precedes the predicted time to failure. The window is moving because, in one embodiment, the logic repeatedly calculates and updates the linear regression in blocks 624 and 648 with use of the system. The 30-day window establishes an advance notice prior to the predicted failure time in order to allow service to be scheduled before the system is subjected to a component failure. In block 630, the logic checks, at the start of the 30-day window, the pressure trend (e.g., the moving slope of the pressure linear regression analysis in block 648). If a positive pressure slope trend is indicted (e.g., pressure is increasing over time) in block 632, the logic advances to blocks 634 and 636 where the decay in oxygen purity is associated with the health of the sieve beds and an alarm is provided. If a negative pressure slope trend is indicted (e.g., pressure is decreasing over time) in block 638, the logic advances to blocks 640 and 642 where the decay in oxygen purity is associated with the health of the compressor (and/or inlet filter) and an alarm is provided.

In block 650, the logic checks again, at the end of the 30-day window, the pressure trend (e.g., the moving slope of the pressure linear regression analysis in block 648). If a positive pressure slope trend is indicted (e.g., pressure is increasing over time) in block 652, the logic advances to blocks 654 and 656 where the decay in oxygen purity is associated with the health of the sieve beds and an alarm is provided. If a negative pressure slope trend is indicted (e.g., pressure is decreasing over time) in block 658, the logic advances to blocks 660 and 662 where the decay in oxygen purity is associated with the health of the compressor (and/or inlet filter) and an alarm is provided. While this embodiment illustrates checking system health at the start and end of a 30-day window, any appropriate interval can be used, and any number of health checks can be performed. In this manner, the user and/or provider are given specific advance warning of which system component(s) is predicted to fail or has failed.

FIG. 9 illustrates another embodiment of a method and logic 900 for analyzing the health and/or predicted time to failure of system components such as sieve bed(s). Method and logic 900 determine time to failure of a sieve bed(s) based on the pressure/time slope linear regression without the use of oxygen data (though in other embodiments such as that of FIG. 6B oxygen data can also used therewith). The monitored pressure data can be obtained from pressure sensor(s) 224 monitoring the pressure at the exit of the sieve bed(s) and/or entrance to the product tank. Other pressure monitoring locations can be used as well. Method and logic 900 use linear regression (such as that of Formula 2) to determine when (in e.g., hours) sieve bed(s) pressure will reach the high threshold of 34 PSI at which time the system will shut down and fail due to excessive sieve bed pressure. Excessive sieve bed pressure indicates the sieve bed(s) is failing due to any number of factors (e.g., dusting, degradation, moisture, contamination, etc.) An alarm is preferably generated in advance of the predicted time of failure to warn that service is required.

Method and logic 900 start in block 644, which was previously described in connection with FIG. 6B, whereby pressure sensor data associated with the sieve bed(s) is collected at various time(s)/interval(s). In block 648, the pressure/time data is used to generate a pressure linear regression based on Formula 2, as previously described in connection with FIG. 6B. The linear regression is used in block 902 to determine the predicted time to failure (in e.g., hours) for when the sieve bed(s) pressure will reach a threshold value of 34 PSI (other values may also be chosen based on the size, capacity and operating parameters of the system). The threshold represents a pressure (e.g., 34 PSI) that is beyond the normal operating pressure range of the sieve bed(s). In block 904, a 30 day before failure window is determined to provide advance warning of the failing component (e.g., sieve bed(s)). The 30 day window may be a moving window that is updated each time method and logic 900 is performed, which can be at any desired time interval(s) (e.g., upon each startup, every 12 or 24 hours, etc.) In block 908, an alarm is triggered when the system enters the 30 day window to provide a warning that a system component (e.g., sieve bed(s)) is near failure. Hence, a linear regression of pressure/time slope data can be used to determine a predicted time to failure.

FIG. 10 illustrates another embodiment of a method and logic 1000 for analyzing the health and/or predicted time to failure of system components such as sieve bed(s). Method and logic 1000 determine time to failure of a sieve bed(s) based on the oxygen purity linear regression and without the use of pressure data (though in other embodiments such as that of FIG. 6B pressure data can also be used therewith). The monitored oxygen purity (e.g., concentration) data can be obtained from oxygen sensor(s) 226 monitoring the oxygen purity at the exit of the sieve bed(s) and/or entrance to the product tank. Other oxygen monitoring locations can be used as well. Method and logic 1000 use linear regression (such as that of Formula 1) to determine when (in e.g., hours) sieve bed(s) oxygen purity will fall below a threshold of 85%, at which time the system will shut down and fail due to low oxygen purity. Low oxygen purity indicates the sieve bed(s) is failing due to any number of factors (e.g., dusting, degradation, moisture, contamination, etc.) An alarm is preferably generated in advance of the predicted time of failure to warn that service is required.

Method and logic 1000 start in block 622, which was previously described in connection with FIG. 6B, whereby oxygen purity data associated with the sieve bed(s) is collected at various time(s)/interval(s). In block 624, the oxygen purity/time data is used to generate an oxygen purity linear regression based on Formula 1, as previously described in connection with FIG. 6B. The linear regression is used in block 626 to determine the predicted time to failure (in e.g., hours) for when the sieve bed(s) pressure will reach a threshold purity value of 85% (other values may also be chosen based on the size, capacity and operating parameters of the system). The threshold represents an oxygen purity (e.g., 85%) that is below the lower limit of acceptable oxygen purity for the system. In block 628, a 30 day before failure window is determined to provide advance warning of the failing component (e.g., sieve bed(s)). The 30 day window may be a moving window that is updated each time method and logic 1000 is performed, which can be at any desired time interval(s) (e.g., upon each startup, every 12 or 24 hours, etc.) In block 636, an alarm is triggered when the system enters the 30 day window to provide a warning that a system component (e.g., sieve bed(s)) is near failure. Therefore, a linear regression of oxygen purity/time slope data can be used to determine a predicted time to failure.

FIG. 11 illustrates another embodiment of a method and logic 1100 for analyzing the health and/or predicted time to failure of system components such as sieve bed(s). Method and logic 1100 determine the predicted time to failure of a sieve bed(s) based on the sooner time to failure based on a pressure/time slope (FIG. 9) and oxygen purity/time slope (FIG. 10) linear regression analysis. Method and logic 100 obtain the predicted time to failure based on pressure/time slope linear regression analysis from block 902 (FIG. 9) and the predicted time to failure based on oxygen purity/time slope linear regression analysis from block 626 (FIG. 10). In block 1102, the two predicted times to failure are compared and the sooner occurring predicted time to failure is chosen. A 30 day before failure window is set based on the sooner predicted time to failure. In block 1104, an alarm is triggered when the system enters the 30 day window to provide a warning that a system component (e.g., sieve bed(s)) is near failure. Hence, method and logic 1100 is based on the sooner predicted time to failure based on two different linear regression analyses.

Figure 8:
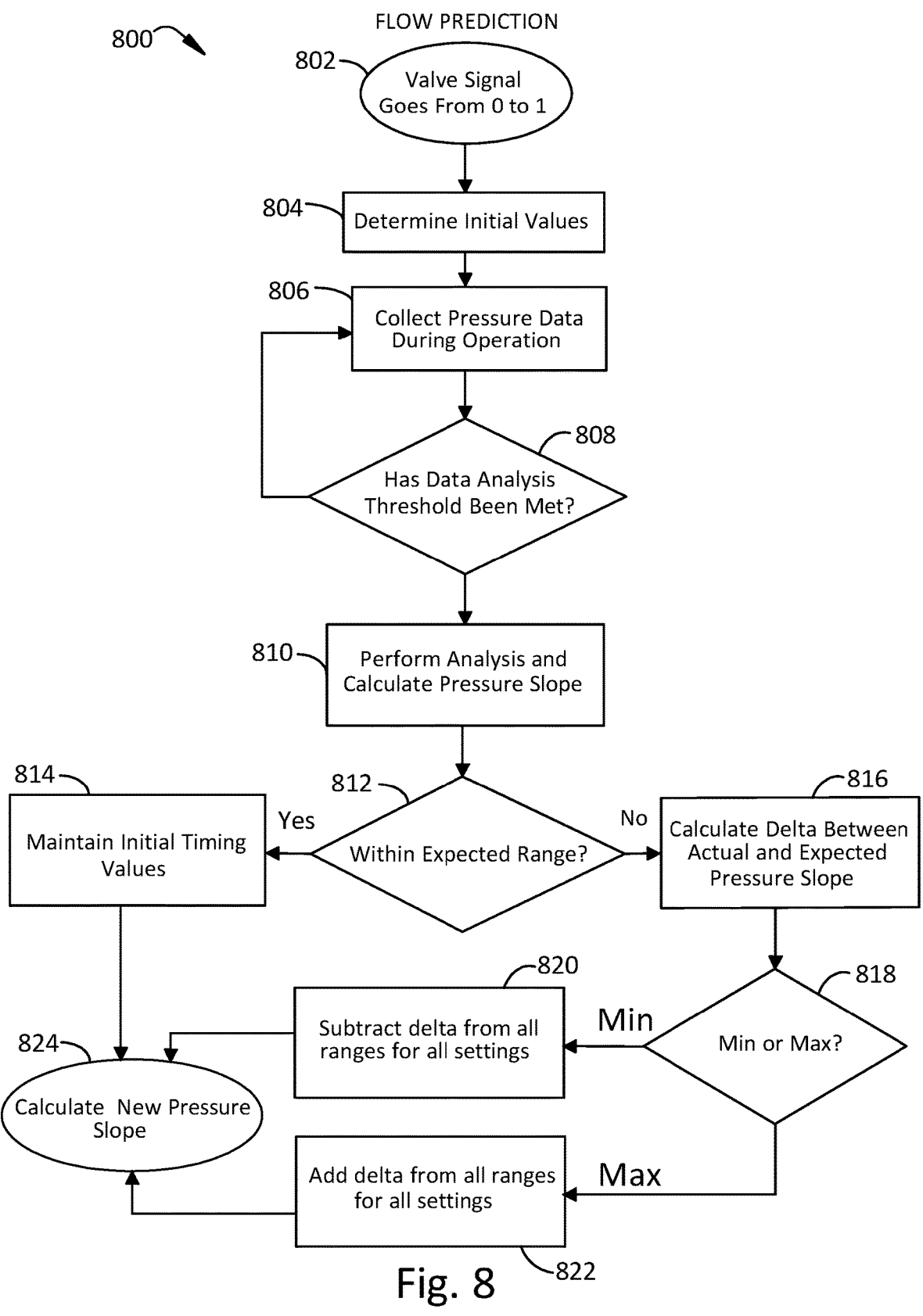
FIG. 8 illustrates one exemplary method to predict an optimal flow rate setting for an oxygen concentrating system.

It is an additional function of the present disclosure that the control system 220 may be further utilized to achieve additional benefits related to optimizing operation based on a flow rate setting for an oxygen concentrating system. FIG. 8 illustrates a method 800 to predict flow rate based on pressure and altitude sensor data or settings. This allows for cost saving by allowing measurement of flow rate through product tank pressure sensor data or feedback instead of requiring a dedicated flow sensor. The measurement of flow exiting the product tank can be used for smart operation of the concentrating system based on a feedback associated with patient need or demand. Smart operation includes reducing energy consumption by running the pump or compressor at a slower speed, reducing system pressures and cycle times, etc. An accurately estimated or determined flow rate can also be displayed on the LED or LCD of the gas concentrating system. And, system performance in terms of patient demand or flow rate can be stored and analyzed for trends at specific settings.

The method 800 begins at block 802 when an air valve (e.g., 204b or 204d) signal goes from 0 to 1 (or open to closed or vice-versa). This valve transition indicates a shift time from high pressure to low pressure for the sieve beds (e.g., 206a or 206b). During such a change or shift, no product gas (e.g., oxygen gas) is flowing to the product tank (e.g., 208a, 208b) from the sieve beds. Thus, at this time, any changes in pressure in the product tank are due to patient demand (or the outflow of product gas to the patient).

At block 804, initial pressure values are determined and stored (e.g., in memory 306). In some embodiments, initial values are determined after a predetermined wait time. Implementing a wait time before recording initial values can prevent recording potentially misleading values due to initial check valve leaks. At block 806, pressure data during operation is collected. Data points may be collected according to a predetermined interval (e.g., every 20 minutes or every 20 1-minute readings; other time intervals can also be sued). In one embodiment, four (4) pressure and time readings are taken and stored in variables "Pressure(X):

set_1" and "time stamp(Y):Time_1" (see also Formula 3 below). At block 808, it is determined if a data analysis threshold has been met. If the data analysis threshold has not been met, the method returns to block 806 to continue pressure data collection. If the threshold has been met, the method proceeds to block 810. At block 810, analysis is performed and a regression analysis is performed using the pressure data. An exemplary linear regression analysis for pressure data is expressed in formula 3.

Calculate the Slope of b of Pressure Readings:

$$\text{Sum}Y = \text{sum}(\text{set\_1})$$

$$\text{Sum}X = \text{sum}(\text{Time\_1})$$

$$XY = \text{set\_1} * \text{Time\_1}$$

$$XX = (\text{Time\_1})^2$$

$$YY = (\text{set\_1})^2$$

$$\text{Sum}XX = \text{sum}(XX)$$

$$\text{Sum}YY = \text{sum}(YY)$$

$$\text{Sum}XY = \text{sum}(XY)$$

$$b = ((4 * \text{Sum}XY) - (\text{Sum}X) * (\text{Sum}Y)) / (4 * (\text{Sum}XX) - (\text{Sum}X)^2)$$

Formula 3: Pressure Decay (Slope)

At block 812, it is determined if the calculated pressure slope b is within a predetermined range (also an average of, for example, five (5) consecutive calculated slopes b can also be used). The predetermined range may be an expected range based on measured conditional factors (e.g., predetermined or expected range=(b<−2.5346) && (b>−2.9577) for a 5 LPM flow setting). If the measured/calculated slope b (or average of the measured/calculated slopes b) is within the expected range, the method proceeds to block 814 where initial timing values are maintained, and the method proceeds to block 824 where a new pressure slope is calculated after each valve change. If the calculated pressure slope is outside the expected predetermined range of slopes for the patient flow setting (e.g., (b<−2.5346) && (b>−2.9577), the method proceeds to block 816. At block 816, the delta between the actual and expected pressure slope is calculated by determining the midpoint of the expected range of slopes (e.g., Midpoint=(minimum+maximum)/2), subtracting that Midpoint from the calculated pressure decay slope (e.g., delta=Midpoint−(calculated slope b)). At block 818, it is determined if the slope b is toward the minimum (i.e., "min") or the maximum (i.e., "max") of the expected pressure slope range. If the slope b is toward the "min," the method proceeds to block 820 where the delta is subtracted from all expected slope ranges for all patient flow settings. If the actual slope is toward the "max," the method proceeds to block 822 where the delta is added for all expected slope ranges for all patient flow settings. At block 824, a new pressure slope b is calculated according to Formula 3 for the new pressure and time readings.

In this manner, the pressure decay in the product tank when no product gas is flowing into the product tank can be used to accurately measure the flow rate of product gas leaving the product tank. This allows a simple pressure sensor to be used along with the logic disclosed herein to provide flow rate measurements. The flow rate measurements can be used to more efficiency run the gas separation system, diagnostic purposes, patient demand trend analysis and usage, etc.

Yet another additional function of the present disclosure is utilizing control system 220 to save energy by utilizing pressure feedback to lower the shifting pressure on the compressor when low flow mode is detected. For example a different valve setting for different flow rates can be detected using linear regression analysis of pressure data. Under lower flow rate settings, power consumption may be reduced. This can increase the life on main components such as the valve, compressor and sieve bed material by lowering the operating pressure of the unit. A further advantage is the reduced temperature on the compressor and its output gas.

While the present inventions have been illustrated by the description of embodiments thereof, and while the embodiments have been described in considerable detail, it is not the intention of the descriptions to restrict or in any way limit the scope of the appended claims to such detail. Additional advantages and modifications will readily appear to those skilled in the art. Therefore, the inventions, in their broader aspects, are not limited to the specific details, the representative apparatus, and illustrative examples shown and described. Accordingly, departures can be made from such details without departing from the spirit or scope of the general inventive concepts.

What is claimed:

1. A method comprising:
collecting oxygen and pressure data from sensors of a gas concentrator;
calculating a linear regression for the pressure data;
determining a predicted time to failure for one or more gas concentrator components based on the collected oxygen data;
determining the slope of the pressure linear regression; and
generating one or more component alarms based on the oxygen data and the pressure linear regression.

2. The method of claim 1, wherein generating one or more component alarms based on the oxygen data and the pressure linear regression comprises:
generating a time window, the time window being a period that ends before the predicted failure of the component.

3. The method of claim 2, wherein generating one or more component alarms based on the oxygen data and the pressure linear regression further comprises:
determining if a slope of the pressure linear regression is positive or negative during the time window.

4. The method of claim 3, wherein generating one or more component alarms based on the oxygen data and the slope of the pressure linear regression further comprises:
generating a sieve bed alarm if the slope of the pressure linear regression is positive at the start of the time window.

5. The method of claim 3, wherein for generating one or more component alarms based on the oxygen data and the slope of the pressure linear regression further comprises:
generating a sieve bed alarm if the slope of the pressure linear regression is positive at the end of the time window.

6. The method of claim 3, wherein generating one or more component alarms based on the oxygen data and the slope of the pressure linear regression further comprises:
generating a compressor alarm if the slope of the pressure linear regression is negative at the start of the time window.

7. The method of claim 3, wherein generating one or more component alarms based on the oxygen data and the slope of the pressure linear regression further comprises:
generating a compressor alarm if the slope of the pressure linear regression is negative at the end of the time window.

8. The method of claim 3, wherein generating one or more component alarms based on the oxygen data and the slope of the pressure linear regression further comprises:
generating a filter alarm if the slope of the pressure linear regression is negative at the start of the time window.

9. The method of claim 3, wherein generating one or more component alarms based on the oxygen data and the slope of the pressure linear regression further comprises:
generating a filter alarm if the slope of the pressure linear regression is negative at the end of the time window.

10. A method comprising:
collecting oxygen and pressure data from sensor of a gas concentrator;
calculating linear regressions for the oxygen and pressure data;
determining a predicted time to failure for one or more gas concentrator components based on the oxygen linear regression;
determining the slope of the pressure linear regression calculation; and
generating one or more component alarms based on the oxygen linear regression and the slope of the pressure linear regression.

11. The method of claim 10, wherein generating one or more component alarms based on the oxygen linear regression and the slope of the pressure linear regression comprises:
using the oxygen linear regression to generate a time window which is a period that ends before the predicted failure of the component.

12. The method of claim 11, wherein generating one or more component alarms based on the oxygen linear regression and the slope of the pressure linear regression further comprises:
determining if the slope of the pressure linear regression is positive or negative during the time window.

13. The method of claim 12, wherein generating one or more component alarms based on the oxygen linear regression and the slope of the pressure linear regression further comprises:
generating a sieve bed alarm if the slope of the pressure linear regression is positive at the start of the time window.

14. The method of claim 12, wherein generating one or more component alarms based on the oxygen linear regression and the slope of the pressure linear regression further comprises:
generating a sieve bed alarm if the slope of the pressure linear regression is positive at the end of the time window.

15. The method of claim 12, wherein generating one or more component alarms based on the oxygen linear regression and the slope of the pressure linear regression further comprises:
generating a compressor alarm if the slope of the pressure linear regression is negative at the start of the time window.

16. The method of claim 12, wherein generating one or more component alarms based on the oxygen linear regression and the slope of the pressure linear regression further comprises:

generating a compressor alarm if the slope of the pressure linear regression is negative at the end of the time window.

17. A method comprising:

collecting oxygen and pressure data;

calculating a linear regression for the pressure data;

determining a first predicted time to failure for one or more gas concentrator components based on the oxygen data;

determining a second predicted time to failure for one or more gas concentrator components based on the pressure linear regression;

comparing the first and second predicted times to failure;

setting based on the comparison a time window having a period that ends before a sooner one of the first predicted time to failure or the second predicted time to failure of the one or more gas concentrator components; and generating one or more component alarms within the time window.

18. The method of claim 17, wherein comparing the first and second predicted times to failure comprises determining which of the first and second predicted times to failure will occur sooner.

19. The method of claim 18, wherein setting a time window based on the comparison comprises setting the time window based on the sooner occurring predicted time to failure.

20. The method of claim 17, wherein generating one or more component alarms within the time window comprises generating one or more component alarms within a 30 day time window.

21. A method comprising:

collecting oxygen and pressure data from sensors of a gas concentrator;

calculating trendline data for the pressure data;

determining a predicted time to failure for one or more gas concentrator components based on the collected oxygen data;

determining the slope of the pressure trendline data; and generating one or more alerts based on the oxygen data and the pressure trendline data.

22. The method of claim 21 wherein calculating trendline data for the pressure data comprises linear regression data.

23. The method of claim 21 wherein calculating trendline data for the pressure data comprises exponential trendline data.

24. The method of claim 21 wherein calculating trendline data for the pressure data comprises logarithmic trendline data.

25. The method of claim 21 wherein calculating trendline data for the pressure data comprises polynomial trendline data.

26. The method of claim 21 wherein calculating trendline data for the pressure data comprises power trendline data.

27. The method of claim 21 wherein generating one or more alerts comprises generating one or more notifications.

28. The method of claim 21 wherein generating one or more alerts comprises generating one or more notifications on a smartphone.

29. The method of claim 21 wherein generating one or more alerts comprises generating one or more notifications over a network.

30. The method of claim 21 wherein generating one or more alerts comprises generating a latest predicted time to failure.

\* \* \* \* \*